US009962558B2

(12) United States Patent
Peyman

(10) Patent No.: US 9,962,558 B2
(45) Date of Patent: *May 8, 2018

(54) METHODS TO REGULATE POLARIZATION AND ENHANCE FUNCTION OF CELLS

(71) Applicant: Gholam A. Peyman, Sun City, AZ (US)

(72) Inventor: Gholam A. Peyman, Sun City, AZ (US)

(*) Notice: Subject to any disclaimer, the term of this patent is extended or adjusted under 35 U.S.C. 154(b) by 0 days. days.

This patent is subject to a terminal disclaimer.

(21) Appl. No.: 14/069,965

(22) Filed: Nov. 1, 2013

(65) Prior Publication Data

US 2014/0056815 A1    Feb. 27, 2014

Related U.S. Application Data

(63) Continuation-in-part of application No. 13/952,875, filed on Jul. 29, 2013, and a continuation-in-part of application No. 13/772,150, filed on Feb. 20, 2013, now Pat. No. 8,562,660, and a continuation-in-part of application No. 13/367,984, filed on Feb. 7, 2012, now Pat. No. 8,460,351, and a continuation-in-part of application No. 13/088,730, filed on Apr. 18, 2011, now Pat. No. 8,409,263, and a continuation-in-part of application No. 11/197,869, filed on Aug. 5, 2005, now Pat. No. 8,388,668.

(51) Int. Cl.
| | |
|---|---|
| *A61N 5/06* | (2006.01) |
| *A61K 41/00* | (2006.01) |
| *A61K 48/00* | (2006.01) |
| *A61K 45/06* | (2006.01) |
| *A61K 49/00* | (2006.01) |
| *A61K 49/08* | (2006.01) |
| *A61K 9/00* | (2006.01) |
| *A61K 9/16* | (2006.01) |
| *A61K 9/51* | (2006.01) |
| *A61F 9/00* | (2006.01) |
| *A61K 31/7105* | (2006.01) |
| *A61K 31/713* | (2006.01) |
| *A61F 9/007* | (2006.01) |
| *A61N 1/36* | (2006.01) |
| *A61N 1/372* | (2006.01) |
| *B82Y 5/00* | (2011.01) |
| *B82Y 30/00* | (2011.01) |

(52) U.S. Cl.
CPC ............ *A61N 5/062* (2013.01); *A61F 9/0017* (2013.01); *A61K 9/0009* (2013.01); *A61K 9/0048* (2013.01); *A61K 9/1611* (2013.01); *A61K 9/5115* (2013.01); *A61K 31/713* (2013.01); *A61K 31/7105* (2013.01); *A61K 41/0047* (2013.01); *A61K 45/06* (2013.01); *A61K 48/0033* (2013.01); *A61K 49/00* (2013.01); *A61K 49/0067* (2013.01); *A61K 49/085* (2013.01); *A61F 9/00727* (2013.01); *A61N 1/36046* (2013.01); *A61N 1/37205* (2013.01); *B82Y 5/00* (2013.01); *B82Y 30/00* (2013.01)

(58) Field of Classification Search
None
See application file for complete search history.

(56) References Cited

U.S. PATENT DOCUMENTS

| | | | |
|---|---|---|---|
| 5,220,181 A | 6/1993 | Kanal et al. | |
| 6,552,053 B2 | 4/2003 | Sun et al. | |
| 6,566,595 B2 | 5/2003 | Suzuki et al. | |
| 6,641,553 B1 | 11/2003 | Chee et al. | |
| 2003/0014089 A1 | 1/2003 | Chow et al. | |
| 2003/0022374 A1 | 1/2003 | Greenbaum et al. | |
| 2004/0003839 A1 | 1/2004 | Curtain | |
| 2005/0004625 A1 | 1/2005 | Chow | |
| 2006/0173362 A1* | 8/2006 | Toms et al. | 600/478 |
| 2010/0185260 A1 | 7/2010 | Olson | |
| 2010/0211146 A1 | 8/2010 | Strowbridge et al. | |
| 2011/0224145 A1* | 9/2011 | Greenberg et al. | 514/17.7 |
| 2011/0270153 A1 | 11/2011 | Olson | |
| 2014/0148880 A1* | 5/2014 | Deisseroth et al. | 607/100 |

OTHER PUBLICATIONS

He et al., Angew. Chem. Int. Ed., 2011, 50: 3080-3083.*
Templeton, article in Pittsburgh Post-Gazette, Apr. 10, 2007.*
Algar et al., Anal. Chem, 2009, 10: 4113-4120.*
Mulder et al., Angiogenesis, 2010, 13: 131-134.*
Joerez et al., Ophthalmology, 2008, 115: 347-354.*
Singerman, Retina, 2009, 29: S49-50; Abstract.*
Min et al., Current Eye Research, 2009, 34: 401-410.*
Baker et al., Angew. Chem. Int. Ed. , 2010, 49: 6726-6744.*
Rhodopsin-like family.*
Yamamoto et al., IEEE Trans Nanobioscience, 2007, 6: 94-98; Abstract.*
Campochiaro, Human Gene Therapy, 2011, 22: 523-529.*
Barakat et al., Expert Opin. Invest. Drugs, 2009, 18: 637-646; Abstract.*
Qiao et al., Journal of Nanomaterials, 2010, p. 1-9.*
Takeda et al., Nature, 2009, 460: 1-16.*
Neuberger et al., Journal of Magnetism and Magnetic Materials, 2005, 293: 483-496.*
Baio et al., Magn. Reson. Mater. Phys., 2006, 19: 313-320.*
Koirala et al., Biomaterials, 2011, 32: 9483-9493.*
Bakalova et al., "Quantum Dot-Conjugated Hybridization Probes for Preliminary Screening of siRNA Sequences" J. Am. Chem. Soc., (2005), 127 (32), pp. 11328-11335.
Derfus et al. "Targeted Quantum Dot Conjugates for siRNA Delivery" Bioconjugate Chem.,vol. 18, No. 5 (2007) pp. 1391-1396.

(Continued)

*Primary Examiner* — Ileana Popa
(74) *Attorney, Agent, or Firm* — The Law Office of Patrick F. O'Reilly III, LLC

(57) ABSTRACT

Minimally invasive delivery with intercellular and/or intracellular localization of nano- and micro-particle solar cells within and among excitable biological cells to controllably regulate membrane polarization and enhance function of such cells. The cells include retinal and other excitable cells.

29 Claims, 2 Drawing Sheets

(56) References Cited

OTHER PUBLICATIONS

Deisseroth "Optogenetics" Nature Methods, Published online Dec. 20, 2010, available at http://www.stanford.edu/group/dlab/papers/deisserothnature2010.pdf.

Dixit et al. "Quantum Dot Encapsulation in Viral Capsids" Nano Letters, vol. 6, No. 9 (2006), pp. 1993-1999.

Ebenstein et al. "Combining atomic force and fluorescence microscopy for analysis of quantum-dot labeled protein-DNA complexes" J. Molecular Recognition, vol. 22, issue 5 (2009), pp. 397-402.

Gill et al. "Fluorescence Resonance Energy Transfer in CdSe/ZnS—DNA Conjugates: Probing Hybridization and Dna Cleavage" J. Phys. Chem. B, vol. 109, (2005), pp. 23715-23719.

Joo et al. "Enhanced Real-Time Monitoring of Adeno-Associated Virus Trafficking by Virus—Quantum Dot Conjugates" ACS Nano, vol. 5, No. 5 (2011), pp. 3523-3535.

Lim et al. "Specific Nucleic Acid Detection Using Photophysical Properties of Quantum Dot Probes" Anal. Chem., vol. 82, No. 3 (2010), 886-891.

Mossman "Quantum dots track who gets into cell nucleus" Physorg.com, Sep. 2, 2010, available at http://www.physorg.com/news202628740.html.

Wang et al. Nucleic Acid Conjugated Nanomaterials for Enhanced Molecular Recognition. ACS Nano 3 (2009) 2451-2460.

You et al. "Incorporation of quantum dots on virus in polycationic solution" Int. J. Nanomedicine, vol. 1, No. 1 (2006), pp. 59-64.

Anscombe "Quantum Dots: Small Structures Poised to Break Big" Photonics Spectra, Jul. 2005, pp. 94-96.

Mali et al. "Intravitreous Injection of a Membrane Depolarization Agent Causes Retinal Degeneration Via Matrix Metalloproteinase-9" Investigative Ophthalmology and Visual Science, vol. 46, No. 6 (2005), pp. 2125-2132.

Greenbaum et al. "Application of Photosynthesis to Artificial Sight" paper presented at the Nanoscale Science and Technology in Medicine Symposium, 23rd International Conference of the IEEE Engineering in Medicine and Biology Society, Oct. 25-28, 2001, Istanbul, Turkey, vol. 4, pp. 4089-4091.

Aylott "Optical nanosensors—an enabling technology for intracellular measurements" Analyst, vol. 128 (2003), pp. 309-312.

Buck et al. "Optochemical nanosensor PEBBLEs: photonic explorers for bioanalysis with biologically localized embedding" Current Opinion in Chemical Biology, vol. 8 (2004), pp. 540-546.

Fehr et al. "Development and use of fluorescent nanosensors for metabolite imaging in living cells" Biochemical Society Transactions, vol. 23, part 1 (2005), pp. 287-290.

Ferreira et al. "Downstream processing of plasmid DNA for gene therapy and DNA vaccine applications," Tibtech, vol. 18 (2000), pp. 380-387.

Fei et al. "Glucose nanosensors based on redox polymer/glucose oxidase modified carbon fiber nanoelectrodes" Talanta, vol. 65 (2005), pp. 918-924.

Haes et al. "A unified view of propagating and localized surface plasmon resonance biosensors" Anal. Bioanal. Chem, vol. 379 (2004), pp. 920-930.

Cullum et al. "The development of optical nanosensors for biological measurements" Tibtech, vol. 18 (2000), pp. 388-393.

Hauser and Zhang, "Peptides as biological semiconductors," Nature, vol. 468 (2010), p. 516.

Audero et al. Sporadic Autonomic Dysregulation and Death Associated with Excessive Serotonin Autoinhibition. Science, vol. 321 (2008), pp. 130-133.

De Crespigny et al. Magnetic Resonance Imaging Assessment of Cerebral Hemodynamics During Spreading Depression in Rats. Journal of Cerebral Blood Flow and Metabolism, vol. 18 (1998), pp. 1008-1017.

Höhne et al. Acetazolamide prevents hypoxic pulmonary vasoconstriction in conscious dogs. J. Appl. Physiol. vol. 97 (2004), pp. 515-521.

Rio-Portilla et al. REM Sleep POST-EYE Movement Activation. International Journal of Bioelectromagnetism, vol. 10, No. 4 (2008), pp. 192-208.

Zhang et al. Organ-specific gene expression in the rhesus monkey eye following intravenous non-viral gene transfer. Molecular Vision 9 (2003) 465-72.

U.S. Appl. No. 13/952,875, filed Jul. 29, 2013.
U.S. Appl. No. 13/772,150, filed Feb. 20, 2013.
U.S. Appl. No. 13/367,984, filed Feb. 7, 2012.
U.S. Appl. No. 13/088,730, filed Apr. 18, 2011.
U.S. Appl. No. 11/197,869, filed Aug. 5, 2005.

* cited by examiner

METHODS TO REGULATE POLARIZATION AND ENHANCE FUNCTION OF CELLS

This application is a Continuation-In-Part of co-pending application U.S. Ser. No. 13/952,875 filed Jul. 29, 2013; which is a Continuation-In-Part of U.S. Ser. No. 13/772,150 filed Feb. 20, 2013 now U.S. Pat. No. 8,562,660; which is a Continuation-In-Part of U.S. Ser. No. 13/367,984 filed Feb. 7, 2012 now U.S. Pat. No. 8,460,351; which is a Continuation-In-Part of application Ser. No. 13/088,730 filed Apr. 18, 2011 now U.S. Pat. No. 8,409,263; which is a Continuation-In-Part of application Ser. No. 11/197,869 filed Aug. 5, 2005 now U.S. Pat. No. 8,388,668; each of which is expressly incorporated by reference herein in its entirety.

FIELD OF THE INVENTION

The invention relates to combined methods to regulate polarization and enhance function of excitable cells.

DETAILED DESCRIPTION

Figure 1:
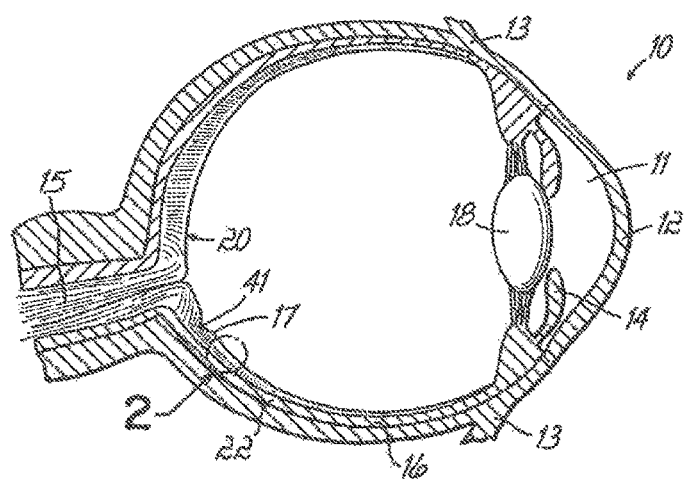
FIG. 1 is a drawing of a longitudinal section of a human eye.

Combination mechanisms to correct, reduce, and/or prevent physiological electro-sensory damage or electromotor damage and promote functional recovery of excitable cells, e.g., neurons in the central nervous system (i.e., brain and spinal cord) and neuronal cells involved with visual, auditory, vocal, olfactory responses, e.g., retinal cells in the eye, cochlear cells in the ear, olfactory cells in the nose, etc., and neurons in the peripheral nervous system are provided. The inventive combination methods can be thought of as akin to combination approaches in treating neoplastic lesions, but targeting less than optimally-functioning excitable cells.

In one embodiment, the combined method promotes functional recovery and controllably regulates plasma membrane polarization of a functional excitable neuronal cell. A biomolecule effecting gene therapy is administered into an eye and/or central nervous system of a patient in need of the therapy (e.g., a patient with a neuronal disease). Quantum dots are administered into the eye and/or central nervous system of the patient, either simultaneously or sequentially either before or after the biomolecule is administered. Light is applied to the eye or central nervous system to controllably activate the quantum dots by controlling exposure time, exposure intensity, exposure site, etc. to controllably regulate the plasma membrane polarization of the functional excitable neuronal cells and to provide the biomolecule to the neuronal cells. In one embodiment, the biomolecule is directly or indirectly associated with, or covalently conjugated to, the quantum dots so that in a single administration (e.g., one injection), both biomolecule and quantum dots components are provided to the patient. Once administered, the quantum dots can be imaged, tracked, monitoring, evaluated in the patient using a sensor or other tracking agent using methods well known in the art (e.g., digital imaging, etc.).

The light sensitive molecules may be provided to specific neurons for therapy. As one example, they may be provided to an optic nerve for retinal therapy. As another example, they may be provided to an olfactory nerve for nasal nerve therapy, and/or as an point of entry for brain therapy, etc. As another example, they may be provided to selective or non-selective sites for selective stimulation of various regions, either alone or in combination. As non-limiting examples of selective stimulation of central nervous system nerves, the visual cortex can be stimulated through specific light stimulation of the retina, the olfactory neuron can be stimulated by smell, the auditory neuron can be stimulation by sound, etc. As non-limiting examples of selective stimulation of peripheral nervous system nerves, chronic pain may be controlled by direct stimulation of the appropriate nerves, and appetite may be suppressed by direct stimulation of appropriate nerves.

Stimulation by light may be achieved by several mechanisms, as known to one skilled in the art. For example, using activation of quantum dots in the brain as an exemplary, non-limiting example, activation may be provided by a fiber optic device surgically placed at the desired area of the brain, located under the scalp, and illuminated by a light source, e.g., a light emitting diode (LED) through a small window made in the skull replaced by clear glass at a desired area. Such a window may remain hidden under the skin, because it is known that light can penetrate a few millimeters into skin. An analogous concept may be used for stimulating other areas of the central nervous system, the peripheral nervous system, or heart or other muscles, with or without application of a fiber optic device if quantum dots are injected through an opening into the superficial area of the brain, nerve, heart muscle, etc. Such stimulation may controllably regulate, i.e., activate/deactivate, by using an appropriate wavelength of light, with or without a processor with the specific neuronal code as pulses. Quantum dots may be used in conjunction with stem cell therapy or in conjunction with other devices, e.g., prosthetic devices, that are activated or otherwise rely or light and/or electrical current.

In addition to using the method for the above indications and for treatment of retinal degeneration, etc. and posttraumatic epilepsy, the method also has applications in amelioration of the underlying pathology and/or symptoms of genetic and/or degenerative diseases, e.g., retinitis pigmentosa, retinal degeneration, central nervous system pathologies such as Alzheimer's disease and Parkinson disease, dopamine-regulated disorders such as migraines, autism, mood disorders, schizophrenia, senile dementia, sleep disorders, restless leg syndrome, and depression. Tourette syndrome, restless leg syndrome, and stuttering are a part of the same spectrum of diseases characterized by malfunctioning membrane potential and electrical pulse transmission. The consequences of infectious diseases, epilepsy, paralysis, and traumatic injury of the brain and/or peripheral nerves are also amenable to therapy with the inventive method. All such disorders can be influenced either with quantum dot administration alone or with medication modifying cell membrane potential, e.g., carbonic anhydrase inhibitors. Amelioration includes any reduction in the signs, symptoms, and/or etiology, including but not limited to prevention, therapy, and curative effects, of any of the above indications. As one example, quantum dots may be targeted to dopamine-regulated nerves for therapy of migraines, mood disorders, etc. As another example, quantum dots can be used for deep subthalamic, cerebral, or cortical and peripheral nerve stimulation for therapy of Parkinson's disease, etc.

A viral vector (e.g., adenovirus, adeno-associated virus, retrovirus) can provide the biomolecule, which can be a natural or synthetic protein, peptide, nucleic acid, oligonucleotide, etc. when conjugated with quantum dots. In one embodiment, the biomolecule is a cell membrane channel protein. If the same wavelength of light stimulates both quantum dots and protein (or other biomolecule), the result is an enhanced action potential in the excitable cells, i.e., this embodiment achieves a synergistic effect. If a different wavelength of light stimulates the quantum dots and protein (or other biomolecule), the result is a subsequent action potential in the excitable cells, i.e., this embodiment achieves silencing of the action potential in the cell. In both cases, the "tunable" selection of the biomolecule and the quantum dots, as well as the specific excitation energy (typically light but also ultrasound radiation energy can be used) applied, provides a controlled and regulated process. In turn, the high degree of control enhances efficacy and safety and permits close monitoring and regulation.

Delivery and intercellular and/or intracellular localization of nano- and micro-particle solar cells within and/or among excitable biological cells to regulate membrane polarization of biological cells combined with other methods to promote functional recovery of damaged excitable cells in the eye and central nervous system. The inventive method provides solar cells in a minimally invasive procedure into the eye, heart, and/or the central nervous system; the solar cells are not implanted in the body in an invasive procedure. The inventive method provides a plurality of solar cells as discrete individual particles; the solar cells are not connected as a unit and do not have a backing layer or backing material. The inventive method uses solar cells that may be activated by ambient light; the method does not use an electrical apparatus and thus does not use photodiodes, stimulating electrodes, or other electrical devices. The inventive method uses solar cells to enhance the regulation of polarization by the excitable biological cells themselves; the solar cells facilitate or boost the ability of excitable biological cells to normalize or regulate their own polarity. The inventive method provides for excitable biological cells to regulate their own polarity; stimulation of the solar cells used in the invention does not generate an action potential to regulate polarity, but instead facilitates the biological cells themselves to regulate polarity. The inventive method provides quantum dots in combination with therapies to enhance functional recovery of neuronal cells damaged by different etiologies, including genetic disorders, ischemic or vascular damage, and age-related damage. By combining modulation of cell polarization, which takes advantage of the ability to regulate quantum dots, with genetic and other approaches to therapy, neuronal degenerative process are ameliorated.

Biological cells are bound by a plasma membrane. In all cells, this membrane has a resting potential. The resting potential is an electrical charge across the plasma membrane of the non-excited or resting cell, rendering the interior of the cell negative with respect to the exterior. Hence, the plasma membrane of all biological cells in their resting state is polarized.

The extent of the resting potential varies among different cell types. In cells such as nerve, muscle, and retinal cells, which are excitable in that they can be stimulated to create an electric current, the resting potential is about −70 millivolts (my). This resting potential arises from two components of the plasma membrane: the sodium/potassium ATPase, which pumps two potassium ions ($K^+$) into the cell for every three sodium ions ($Na^+$) it pumps out of the cell, and "leakiness" of some $K^+$ channels, allowing slow facilitated diffusion of $K^+$ out of the cell. The result is a net loss of positive charge from within the resting cell.

Certain external stimuli reduce the charge across the plasma membrane, resulting in membrane depolarization. As one example, mechanical stimuli (e.g., stretching, sound waves) activate mechanically-gated $Na^+$ channels. As another example, certain neurotransmitters (e.g., acetylcholine) open ligand-gated $Na^+$ channels. In each case, the facilitated diffusion of $Na^+$ into the cell depolarizes the membrane; it reduces the resting potential at that membrane location. This creates an excitatory postsynaptic potential (EPSP).

If the potential at any membrane location is reduced to the threshold voltage, many voltage-gated $Na^+$ channels open in that location, generating an influx of $Na^+$. This localized, sudden, complete depolarization opens adjacent voltage-gated $Na^+$ channels. The result is a wave of depolarization along the cell membrane, referred to as the action potential or, in excitable cells, an impulse.

A second stimulus applied to an excitable cell within a short time (less than 0.001 second) after the first stimulus will not trigger another impulse. This is because the membrane is depolarized, leaving the cell in a refractory period. Only when the −70 my polarity is reestablished, termed repolarization, will an excitable cell be able to respond to another stimulus. Repolarization is established by facilitated diffusion of $K^+$ out of the cell. When the cell is finally rested, $Na^+$ that entered the cell at each impulse are actively transported back out of the cell.

Hyperpolarization occurs when negatively charged chloride ions ($Cl^-$) enter the cell and $K^+$ exit the cell. Some neurotransmitters may facilitate this by opening $Cl^-$ and/or $K^+$ channels in the plasma membrane. Hyperpolarization results in an inhibitory postsynaptic potential (IPSP); although the threshold voltage of the cell is unchanged, it requires a stronger excitatory stimulus to reach threshold.

Abnormal cell polarization may affect regenerative and/or functional process of excitable cells, and result in cell dysfunction. Abnormal cell polarization includes, but is not limited to, any of the following and whether transient or sustained: loss of polarization, decreased polarization, altered polarization, hyperpolarization, and any deviation from normal cell polarization. Excitable cells include, but are not limited to, sensory cells (e.g., retina and macula of the eye), neuronal cells in the central nervous system (CNS) (brain and spinal cord) and peripheral nervous system, muscle cells (striated, cardiac, and smooth muscle cells).

The orientation of the cell with respect to its apical, lateral, and basal surfaces may affect polarization and may be regulated by the inventive method. Adjacent cells communicate in the lateral domain, with attachment or contact sites by which cells adhere to one another. Terminal bars, attachment sites between cells that act as a barrier to passage of substances, are located around the entire circumference of cells and are composed of junctional complexes responsible for joining individual cells. Occluding junctions, also referred to as tight junctions or zonula occludentes, are located apically within the lateral domain and encircle the cell, separating the luminal region from the intercellular space and cytoplasm. These are narrow regions of contact between the plasma membranes of adjacent cells and seal off the intercellular space, forming an impermeable diffusion barrier between cells and preventing proteins from migrating between apical and lateral surfaces of the cell. In one embodiment, the method selectively regulates polarization in areas of the cell bound by occluding junctions. Particles may be selectively positioned and/or selectively regulated to regulate polarization at a desired site.

Ischemic cell death is caused by failure of the ionic pumps of the plasma membrane. Depolarization of the plasma membrane in retinal cells and subsequent synaptic release of L-glutamate are implicated in ischemic retinal damage. Mali et al. (Investigative Ophthalmology and Visual Science, 2005, 46, 2125) reported that when KCl, a known membrane depolarizing agent, is injected into the vitreous humor, the subsequent membrane depolarization results in a dose- and time-related upregulation of matrix metalloproteinase (MMP)-9 activity and protein in the retina. This was associated with an increase in proapoptotic protein Bax and apoptotic death of cells in the ganglion cell layer and inner nuclear layer, and subsequent loss of NF-L-positive ganglion cells and calretinin-positive amacrine cells. A synthetic MMP inhibitor inhibited KCl-mediated MMP-9 upregulation, which led to a significant attenuation of KCl-induced retinal damage. Regulating polarization thus inhibits MMP-9 and decreases damage that can diminish visual acuity.

Methods to regulate membrane polarization of excitable cells assist in minimizing physiologic damage and reducing pathology including but not limited to ischemic damage to the retina, degenerative diseases of the retina including but not limited to retinitis pigmentosa, ischemic and/or degenerative diseases of cardiac muscle, and/or ischemic and degenerative diseases of cerebral tissue, etc. In turn, the method minimizes or prevents undesirable effects such as loss of visual acuity, myocardial infarction, cerebral stroke, etc. and enhances a patient's quality of life.

The inventive method may be more fully appreciated with respect to its utility in a single organ, such as the eye. One skilled in the art will realize, however, that it is not so limited and is applicable to other excitable cells.

In one embodiment, the inventive method externally administers to a patient a composition or, alternatively a device in a biocompatible composition, comprising quantum dots or solar cells to stimulate the cell membranes from inside of the cell or outside of the cell of all retinal cells. In one embodiment, the quantum dots injected into the eye and are delivered to the retinal cell cytoplasm or nucleus. In one embodiment, the quantum dots are introduced into the central nervous system. In one embodiment, the quantum dots are conjugated or otherwise associated with proteins or other moieties and provided using a vector to a patient to effect functional recovery of neuronal cells. One non-limiting example of this embodiment is quantum dots conjugated with a channel proteins introduced via a viral vector (e.g., adeno-associated virus (AAV)) to effect retinal gene therapy. Such a vector and/or quantum dots can be labeled for visualization, tracking, sensing, etc. For example, the quantum dots can be labeled or tagged with a signal recognition moiety. Such a vector can incorporate quantum dots into the viral capsid using, e.g., (poly)ethylene glycol (PEG) moieties. Another non-limiting example is the use and selective regulation, selective activation/deactivation alone or in combination, to monitor interfering RNA (RNAi) delivery and regulate gene silencing. Another non-limiting example is the use of quantum dots for in situ visualization of gene expression. This may be performed using quantum dot-DNA-coated polymer. Combinations of these embodiments are contemplated and included, using methods known by one skilled in the art and as subsequently described.

As used herein, particles, quantum dots, and solar cells are used synonymously.

The retinal cells comprise at least ganglion cells, glial cells, photoreceptor cells, Muller cells, bipolar cells, horizontal cells, microglial cells, and cells of the neural fibers, etc. The amount of stimulation, or degree of membrane stimulation, can be regulated by the amount of energy provided by the particles. The total amount of energy provided by the particles to transmit to the membrane depends upon the time of particle activation.

The particles are activated by the energy source; the response to the specific wavelength depends on the inner material building the inner semiconductor. The energy source to activate the particles provides ambient light, ultraviolet light, visible light, infrared light, or ultrasound radiation. In one embodiment, the particles respond to blue, red, green, or IR light. In one embodiment, a plurality of particles respond to various specific wavelengths. In one embodiment, the particles have multiple semiconductor cores, and thus respond to various wavelengths. The wavelength selections are photons with different energies. The particles must have energy bandgaps or energy statues that match the energy of the photons. One skilled in the art tunes the energy levels using materials with different band-gaps or by carefully selecting the quantum size as it effects the energy level. Thus, one uses different size particles and/or particles with different cores. In one embodiment, the activation time interval ranges from 1 nanosecond to 100 nanoseconds. In one embodiment, the activation time interval ranges from 1 second to 100 seconds.

The source of energy activates the particles for the particles to provide sufficient energy to activate the membrane. In one embodiment, the energy source sufficient to activate the particles ranges from about one picojoule to one microjoule. In one embodiment, the activation energy source is external ambient light. In one embodiment, the activation energy source is a diode, LED, etc. Other activation energy sources are possible, as known by one skilled in the art. The energy source provides electromagnetic radiation, as known to one skilled in the art. Electromagnetic radiation includes infrared radiation (700 nm to 1 mm), visible light (380 nm to 760 nm), and ultraviolet radiation (4 nm to 400 nm). The energy source is varied to vary the response of the particles; as one skilled in the art is aware, the shorter the wavelength, the more energy is delivered. As an example, infrared wavelengths (thermal activation), visible and ultraviolet wavelengths are provided for activating the particles to produce the desired photovoltaic (energy) response from the particle by a separate energy source or one that can provide combinations of the required wavelength ranges. The energy source(s) may be externally programmed (such as by computer software) to produce different wavelengths resulting in photovoltaic responses at desired time intervals. The regulation or control of the timed production of generated photovoltaic responses from the particles can be used to control the regulation of cell membrane potentials. The energy input from the energy source may be varied to vary the particles responses, hence regulating and/or controlling the membrane potential. The particles respond to the specific wavelength(s) to which they are exposed. A specific coating to the particles renders them specific. The protein coating can direct them to attach to certain cell membranes, and/or to enter a cell such as a normal cell, a tumor cell, a nerve cell, a glial cell, The particles, albeit relatively non-selective, can potentially increase the membrane potential of any cells to which they come into contact. After exposure to light, a diode, etc. they emit an electrical potential, current, or fluorescence. The electrical potential generated by this exposure to radiation increases the cell membrane potential.

FIG. 1 shows a mammalian eye 10. The structures and locations of the anterior chamber 11, cornea 12, conjunctiva 13, iris 14, optic nerve 15, sclera 16, macula lutea or macula 17, lens 18, retina 20, choroid 22, and fovea 41 are indicated. The macula is located in the center of the posterior part of the retina 20 and is the most sensitive portion of the retina. It is an oval region of about 3 mm by 5 mm, in the center of which is a depression, the fovea centralis 41, from which rods are absent. Inside the fovea 41 is the point of entrance of the optic nerve 15 and its central artery. At this point, the retina 20 is incomplete and forms the blind spot.

Figure 2:
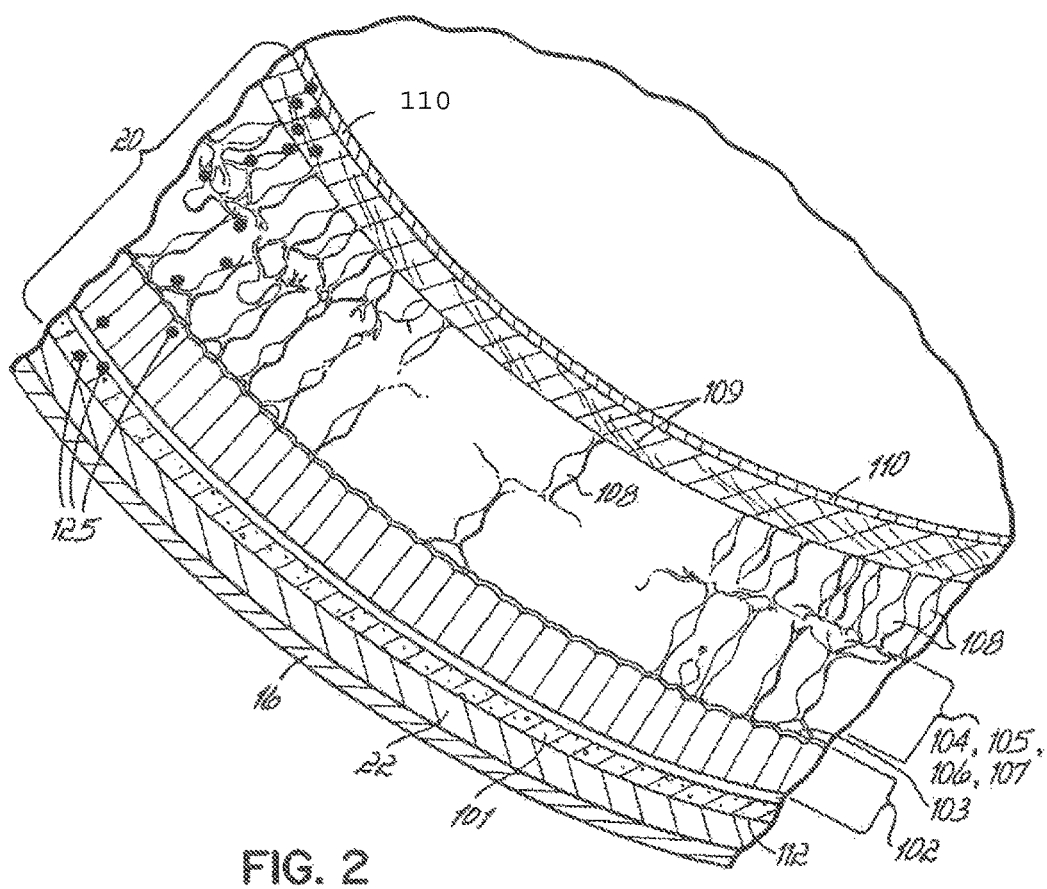
FIG. 2 is an enlarged diagrammatic illustration of the circled area 2 of FIG. 1 showing detailed retinal structures.

The encircled area 2 of FIG. 1 is shown in exploded form in FIG. 2. As shown in FIG. 2, the retina 20 forms the innermost layer of the posterior portion of the eye and is the photoreceptor organ. The retina 20 has an optical portion that lines the inner surface of the choroid 22 and extends from the papilla of the optic nerve 15 to the ora serrata 21 anteriorly. At the papilla, where the retina 20 stops, and at the ora serrata 21, the retina 20 is firmly connected with the retinal pigment epithelium (RPE) 101.

The retina 20 has ten parallel layers. These are, from the choroid in, as follows: the RPE 101, photoreceptor cells (rod and cone inner and outer segments) 102, the external limiting membrane 103, the outer nuclear layer 104, the outer plexiform layer 105, the inner nuclear layer 106, the inner plexiform layer 107, the layer of ganglion cells 108, the layer of optic nerve fibers or neurofiber layer 109, and the internal limiting membrane 110. The internal limiting membrane 110 is very thin (less than 5 µm), and normally adheres with the neurofiber layer 109 of the ganglion cells 108.

The pigment epithelial cell layer or RPE 101 rests on a basal lamina termed Bruch's membrane 112 that is adjacent to the choroid 22.

The next three layers are composed of various portions of one cell type, termed the first neuron. These layers are the photoreceptor region (lamina) 102 of rods and cones, the external limiting membrane 103, and the outer nuclear layer 104 composed of the nuclei of the rods and cones cells. The rods have long, thin bodies, and the cones have a broad base. The rods have greater sensitivity for low light levels; the cones have better visual acuity in daylight and are also responsible for color perception. There are three types of cones, each absorbing light from a different portion of the visible spectrum: long-wavelength (red), mid-wavelength (green), and short-wavelength (blue) light. Both rods and cones contain the transmembrane protein opsin, and the prosthetic group retinal, a vitamin A derivative. The opsins in each cell type contain different amino acids that confer differences in light absorption.

The RPE, photoreceptor cells, external limiting membrane, outer nuclear layer, and outer plexiform layer constitute the neuro-epithelial layer of the retina.

The inner nuclear layer, inner plexiform layer, ganglion cell layer, nerve fiber layer, and internal limiting membrane constitute the cerebral layer of the retina. The inner nuclear layer contains bipolar cells, ganglion cells, horizontal cells, amacrine cells, Muller cells, and astrocytes, the latter two being types of glial cells. The Muller cells have nuclei in the inner nuclear area and cytoplasm extending from the internal limiting membrane 110 to the external limiting membrane 103. The external limiting membrane 103 is a region of terminal bars between Muller's cells and the visual receptors.

The next three layers of the retina are composed of various parts of the second neurons, whose nuclei reside in the inner nuclear layer and whose cytoplasmic processes extend into the outer plexiform layer to synapse with the receptor cells and to the inner plexiform layer to synapse with the ganglion cells. Thus, the second neuron is bipolar.

The third neuron, the multipolar ganglion cells, sends its nerve fiber (axon) to the optic nerve.

The last layer of the retina is the internal limiting membrane (ILM) on which the processes of the Muller's cells rest.

The retina contains a complex interneuronal array. Bipolar cells and ganglion cells are sensory cells that together form a path from the rods and cones to the brain. Other neurons form synapses with the bipolar cells and ganglion cells and modify their activity. For example, ganglion cells, or ganglia, generate action potentials and conduct these impulses back to the brain along the optic nerve. Vision is based on the modulation of these impulses, but does not require the direct relationship between a visual stimulus and an action potential. The visual photosensitive cells, the rods and cones, do not generate action potentials, as do other sensory cells (e.g., olfactory, gustatory, and auditory sensory cells).

Muller cells, the principal type of glial cells, form architectural support structures stretching radially across the thickness of the retina, and forming the limits of the retina at the outer and inner limiting membranes, respectively. Muller cell bodies in the inner nuclear layer project irregularly thick and thin processes in either direction to the outer and inner limiting membranes. These processes insinuate themselves between cell bodies of the neurons in the nuclear layers, and envelope groups of neural processes in the plexiform layers. Retinal neural processes can only have direct contact, without enveloping Muller cell processes, at their synapses. The junctions forming the outer limiting membrane are between Muller cells, and other Muller cells and photoreceptor cells, as sturdy desmosomes or zonula adherens. Muller cells perform a range of functions that contribute to the health of the retinal neurons. These functions include supplying endproducts of anaerobic metabolism (breakdown of glycogen) to fuel neuronal aerobic metabolism; removing neural waste products such as carbon dioxide and ammonia and recycling spent amino acid transmitters; protecting neurons from exposure to excess neurotransmitters using uptake and recycling mechanisms; phagocytosis of neuronal debris and release of neuroactive substances; synthesizing retinoic acid, required in the development of the eye and nervous system, from retinol; controlling homeostasis and protecting neurons from deleterious changes in their ionic environment by taking up and redistributing extracellular $K^+$; and contributing to generation of the electroretinogram (ERG) b-wave, the slow P3 component of the ERG, and the scotopic threshold response (STR) by regulating $K^+$ distribution across the retinal vitreous border, across the whole retina, and locally in the inner plexiform layer of the retina.

Astrocytes, the other type of glial cell, envelope ganglion cell axons and have a relationship to blood vessels of the nerve fiber, suggesting they are axonal and vascular glial sheaths and part of a blood-brain barrier. They contain abundant glycogen, similar to Muller cells, and provide nutrition to the neurons in the form of glucose. They may serve a role in ionic homeostasis in regulating extracellular $K^+$ levels and neurotransmitter metabolism. They have a characteristic flattened cell body and fibrous radiating processes which contain intermediate filaments. The cell bodies and processes are almost entirely restricted to the nerve fiber layer of the retina. Their morphology changes from the optic nerve head to the periphery: from extremely elongated near the optic nerve to a symmetrical stellate form in the far peripheral retina.

Microglial cells are not neuroglial cells and enter the retina coincident with mesenchymal precursors of retinal blood vessels in development, and are found in every layer of the retina. They are one of two types. One type is thought to enter the retina at earlier stages of development from the optic nerve mesenchyme and lie dormant in the retinal layers for much of the life of the retina. The other type appears to be blood-borne cells, possibly originating from vessel pericytes. Both types can be stimulated into a macrophagic function upon retinal trauma, in degenerative diseases of the retina, etc. when they then engage in phagocytosis of degenerating retinal neurons.

All glial cells in the central nervous system (CNS) are coupled extensively by gap junctions. This coupling underlies several glial cell processes, including regulating extracellular $K^+$ by spatial buffering, propagating intercellular $Ca^{2+}$ waves, regulating intracellular ion levels, and modulating neuronal activity.

Activation of retinal glial cells with chemical, mechanical, or electrical stimuli often initiate propagated waves of calcium ions ($Ca^{2+}$). These $Ca^{2+}$ waves travel at a velocity of 23 μm/second and up to 180 μm/second from the site of initiation. The waves travel through both astrocytes and Muller cells, even when the wave is initiated by stimulating a single astrocyte.

$Ca^{2+}$ waves propagate between glial cells in the retina by two mechanisms: diffusion of an intracellular messenger through gap junctions, and release of an extracellular messenger. $Ca^{2+}$ wave propagation between astrocytes is mediated largely by diffusion of an intracellular messenger, likely inositol triphosphate (IP3), through gap junctions, along with release of adenosine triphosphate (ATP). Propagation from astrocytes to Muller cells, and from one Muller cell to other Muller cells, is mediated by ATP release.

Retinal neurons and glial cells also communicate. Muller cells have transient $Ca^{2+}$ increases that occur at a low frequency. Stimulating the retina with repetitive light flashes significantly increases the frequency of these $Ca^{2+}$ transients, most prominent in Muller cell endfeet at the retinal surface, but also in Muller cell processes in the inner plexiform layer. This neuron-to-glial cell communication indicates that glial cell $Ca^{2+}$ transients are physiological responses in vivo.

Stimulated glial cells directly modulate the electrical activity of retinal neurons, leading either to enhanced or depressed neuronal spiking. Inhibitory glial modulation of neuronal spiking may be $Ca^{2+}$-dependent, because the magnitude of neuronal modulation was proportional to the amplitude of the $Ca^{2+}$ increase in neighboring glial cells. Glial cells can modulate neuronal activity in the retina by at least three mechanisms. In some ganglion cells, glial cell activation facilitates synaptic transmissions and enhances light-evoked spiking. In other ganglion cells, there is depressed synaptic transmissions and decreased spiking. Glial cell activation can also result in ganglion cells hyperpolarization, mediated by activating A1 receptors and opening neuronal $K^+$ channels.

Stimulated glial cells also indirectly modulate the electrical activity of retinal neurons. This is mediated by glutamate uptake by Muller cells at synapses by glutamate transporters such as GLAST (EAAT1) and GLT-1 (EAAT2) in Muller cells. When glutamate transport in the retina is blocked, both the amplitude and the duration of ganglion cell EPSCs are increased. Glial cell modulation of electrical activation of retinal neurons is also mediated by regulating extracellular $K^+$ and $H^+$ levels. Neuronal activity leads to substantial variations in the concentration of $K^+$ and $H^+$ in the extracellular space, which can alter synaptic transmission; an increase of $K^+$ depolarizes synaptic terminals, while an increase of $H^+$ blocks presynaptic $Ca^{2+}$ channels and NMDA receptors. Muller cells regulate extracellular concentrations of $K^+$ and $H^+$, thus influencing the effect of these ions on synaptic transmission.

With reference to FIG. 2, one skilled in the art will appreciate that solar cell micro- and/or nano-particles 125, provided selectively or substantially throughout the all regions of the retina, enhance, facilitate or boost the ability of these biological cells to regulate their polarity. This is in contrast to use of a device that supplies an electrical potential, that is implanted in an invasive surgical procedure, that is localized, etc.

Besides pathologies in one or more of the above described mechanisms to maintain and/or regulate retinal cell polarity, other excitable cells besides the retina may have pathologies that occur from defects in cell plasma membrane polarization. As one example, excitable cells in the brain of Alzheimer's patients have abnormal electrical conducting and stabilizing mechanisms, resulting in loss of electrical stimulation. Repolarization of these cells provides additional stimulation to replace the abnormal cell membrane polarization and/or the cell membrane polarization that was diminished or lost. As another example, glial cell scar tissue culminating from epileptic seizures results in abnormal electrical stabilizing mechanisms in excitable cells of the brain. Repolarization of these cells provides a stabilized threshold, resulting in a calming effect. One skilled in the art will appreciate other pathologies for which the inventive method may be used.

The inventive method includes mechanisms to delay, minimize, reduce, alleviate, correct, or prevent electrosensory polarization pathologies. Such mechanisms may attenuate cellular damage resulting from abnormal polarization, reduced polarization, enhanced polarization, hyperpolarization, or loss of polarization. These polarization defects may be of any type and/or cell combination, and may stimulate and/or de-stimulate the cell(s). They may, for example, be transient in one cell type, sustained in one cell type, propagated to affect adjacent cells, propagated along a network to affect non-adjacent cells, etc.

It is known attaching nanocrystal quantum dots to semiconductor layers increases the photovoltaic efficiencies. The semiconductor solar cells work by using the energy of incoming photons to raise electrons from the semiconductor's valence band to its conduction band. A potential barrier formed at the junction between p-type and n-type regions of the semiconductor forces the pairs to split, thereby producing a current, thus influencing, changing, or regulating the polarization of a membrane. The particles are stimulated by using an external or internal energy source. Polarization of the particles is regulated by producing or varying the current. The particles are used to stimulate the cell membrane by varying the input energy from the energy source.

One embodiment provides nano- or micro-sized solar cells to regulate the polarity of excitable cells. As previously described, excitable cells include, but are not limited to, sensory cells such as the retina of the eye, all three types of muscle cells, and central and peripheral system nerve cells. Such nano- or micro-sized solar cells are hereinafter generally referred to as particles 125 as shown in FIG. 2. Particles encompass any and all sizes which permit passage through intercellular and/or intracellular spaces in the organ or area of the organ of interest. For example, intercellular spaces in the retina are about 30 angstroms ($30 \times 10^{-8}$), so that particles for intercellular retinal distribution may be sized for these spaces, as known to one skilled in the art.

The solar cell nano- and/or micro-particles 125 are three dimensional semiconductor devices. The particles use light energy or ultrasound energy to generate electrical energy to provide a photovoltaic effect. In one embodiment, the particle material is a ceramic. In another embodiment, the particle material is a plastic. In another embodiment, the particle material is silicon. Particles of crystalline silicon may be monocrystalline cells, poly or multicrystalline cells, or ribbon silicon having a multicrystalline structure. These are fabricated as microscale or nanoscale particles that are administered to a patient.

The particles may be a nanocrystal of synthetic silicon, gallium/arsenide, cadmium/selenium, copper/indium/gallium/selenide, zinc sulfide, indium/gallium/phosphide, gallium arsenide, indium/gallium nitride, and are synthesized controlling crystal conformations and sizes.

The particles (quantum dots) may also be biocompatible short peptides made of naturally occurring amino acids that have the optical and electronic properties of semiconductor nano-crystals. One example is short peptides of phenylalanine. The particles can consist of both inorganic or organic materials, as previously described.

The particles may be coated with biocompatible mono- or bilayers of phospholipid a protein, a peptide polyethylene glycol (PEG) that can be used as a scaffold to aid in biocompatibility of the particle. The particles can be entirely or partially biodegradable.

In one embodiment, the quantum dots are delivered to the retinal cell cytoplasm or nucleus, regardless of the particular injection site in the eye. In one embodiment, the quantum dots are introduced into the central nervous system, e.g., by injection. In one embodiment, the quantum dots are covalently linked, i.e., conjugated, with natural or synthetic biomolecules (e.g., proteins, peptides, nucleic acids, oligonucleotides, etc.) that introduce a vector (e.g., adeno-associated virus (AAV) for retinal gene therapy. Such a vector and/or quantum dots can be labeled for visualization, tracking, sensing, etc. For example, the quantum dots can be labeled or tagged with a signal recognition moiety. Such a vector can incorporate quantum dots into the viral capsid using, e.g., (poly)ethylene glycol (PEG) moieties. Combinations of these embodiments are contemplated and included in the inventive method, using methods known by one skilled in the art and as subsequently described.

In one embodiment, quantum dots are conjugated with a moiety such as an ocular peptide or protein, to result in a biologically active quantum dot conjugate. Such conjugation allows the therapeutic effect to be controlled and specific, while sensing and tracking the conjugate location, function, etc. in, e.g., the retina.

Examples of such ocular peptides and proteins include, but are not limited to, membrane-bound G-protein coupled photoreceptors (opsins, including the rod cell night vision pigment rhodopsin and cone cell color vision proteins), and members of the family of ocular transport proteins (aquaporins).

In one embodiment, short peptides of naturally occurring amino acids that have the optical and electronic properties of semiconductor nano-crystals are conjugated to quantum dots. One non-limiting example of such a short peptide is (poly)phenylalanine. In these embodiments, the resulting conjugate contains both inorganic and organic materials, as previously described. In one embodiment, the conjugates may be coated with biocompatible mono- or bilayers of phospholipid, protein, and/or a (poly)ethylene glycol (PEG) molecule that can be used as a scaffold to aid in biocompatibility of the particle. Any of these organic moieties may be utilized to ionically, electronically or covalently form the biologically active conjugates. The conjugates are entirely or partially biodegradable.

In one embodiment, a quantum dot conjugated to a vector is capable of modifying an ocular gene, e.g., a gene of a retinal cell. In this embodiment, the quantum dot, besides regulating membrane polarity of an excitable cell such as a retinal cell, also provides therapy to ameliorate or prevent a genetically based retinal disease (e.g., retinitis pigmentosa). In one embodiment, the vector may be a plasmid vector, a binary vector, a cloning vector, an expression vector, a shuttle vector, or a viral vector as known to one skilled in the art. The vector typically contains a promoter, a means for replicating the vector, a coding region, and an efficiency increasing region. In one embodiment, the vector is a virus such as an adenovirus, an adeno-associated virus (AAV), a retrovirus, and other viral vectors for gene therapy, as known to one skilled in the art. As one non-limiting example, quantum dots are functionalized and/or linked to viral vectors using (poly)ethylene glycol (PEG) moieties. The number of PEGS can be varied depending on, e.g., ocular site, need to enhanced hydrophilicity, protein size, etc. The viral vector and quantum dot are combined in the presence of at least one biocompatible adjuvant, suspension agent, surfactant, etc. Quantum dots may be coated with or linked to, e.g., folate, polydopamine, etc. so that these molecules are targeted intracellularly, extracellularly, to a cell membrane, to a specific cellular site or organelle, etc.

Conjugation of quantum dots to viral capsids permits in vivo observation of retinal neurons and the individual glycine receptors in living neurons. A single quantum dot can be recognized by optical coherence tomography (OCT) and can be counted, tracked, assessed, monitored, and evaluated for longevity and efficacy, and hence therapy can also be monitored, over time.

In one embodiment, quantum dots associated with other biomolecules, e.g., conjugated with halorrhodopson, conjugated with a customized virus, are used to regulate, i.e., stimulate or inhibit, action potential of a neuron. Quantum dots can be associated with, e.g., conjugated with, a virus, a virus capsid, a cell penetrating protein, and/or other molecule(s) to stimulate specific neurons or specific neuronal function, or may be provided with appropriate stem cells.

In one embodiment, covalent conjugation may not be required or desired, and in this embodiment quantum dots may be simply associated with a viral vector. In one embodiment, quantum dots may be mixed with an appropriate viral vector in the presence of a cationic polymer, e.g. hexadimethrine bromide POLYBRENE® to form a colloidal complex suitable for introducing into a retinal cell. In one embodiment, quantum dots are tagged with an amide, a thiol, etc. using electrostatic interaction along with functionalizing means known to one skilled in the art.

In one embodiment, the quantum dots that are conjugated or associated with a biomolecule are delivered to a target cell cytoplasm or nucleus, using described methods and/or methods known in the art. In one embodiment, the biomolecule comprises nucleic acid, such as DNA and RNA, as well as synthetic congeners thereof. Non-limiting examples of nucleic acids may include plasmid DNA encoding protein or inhibitory RNA producing nucleotide sequences, synthetic sequences of single or double strands, missense, antisense, nonsense, on and off and rate regulatory nucleotides that control protein, peptide, and nucleic acid production.

Nucleic acids include, but are not limited to, genomic DNA, cDNA, RNAi, siRNA, shRNA, mRNA, tRNA, rRNA, microRNA, hybrid sequences or synthetic or semi-synthetic sequences. Each of these may be naturally occurring or synthetic. Each of these may be of human, plant, bacterial, yeast, viral, etc. origin. Each of these may be any size, e.g., ranging from oligonucleotides to chromosomes. They may be obtained by any technique known to one skilled in the art.

In one embodiment, a nucleotide sequence may also encode products for synthesis or inhibition of a therapeutic protein such as, but not limited to, anti-cancer agents, growth factors, hypoglycemic agents, anti-angiogenic agents, bacterial antigens, viral antigens, tumor antigens, and/or metabolic enzymes. Examples of anti-cancer agents include, but are not limited to, interleukin-2, interleukin-4, interleukin-7, interleukin-12, interleukin-15, interferon-α, interferon-β, interferon-γ, colony stimulating factor, granulocyte-macrophage stimulating factor, anti-angiogenic agents, tumor suppressor genes, thymidine kinase, eNOS, iNOS, p53, p16, TNF-α, Fas-ligand, mutated oncogenes, tumor antigens, viral antigens, and/or bacterial antigens. In one embodiment, plasmid DNA may encode for an RNAi molecule designed to inhibit protein(s) involved in tumor or other hyperproliferative cells' growth or maintenance. In one embodiment, a plasmid DNA may simultaneously encode a therapeutic protein and one or more RNAi molecules. In one embodiment, a nucleic acid may be a mixture of plasmid DNA and synthetic RNA, including sense RNA, antisense RNA, ribozymes, etc.

In one embodiment, the disclosed quantum dot-nucleic acid complex is administered to an individual, e.g., patient in need of such therapy, to ameliorate a genetic disease. In one, embodiment, the disclosed quantum dot-nucleic acid complex is administered to an individual, e.g., a patient with a tumor, to reduce the tumor burden, ameliorate tumor effects, treat the tumor, etc. Therapy may be curative, palliative, remediation, etc. and may be either total or partial, and may be either therapeutic or preventive. The disclosed quantum dot-nucleic acid complex may be used in gene targeting or knockout of specific genes, for e.g., with at least one engineered nuclease, tumor suppressor gene(s), etc. In one embodiment, the disclosed quantum dot-nucleic acid complex contains a wild-type or non-mutated form of a gene or part of a gene, and is introduced into a cell or cells, with the wild-type or non-mutated form of the nucleic acid replacing a defective and/or mutated form of the nucleic acid, e.g., DNA. Because the nucleic acid may be synthetic oligonucleotide, the disclosed gene therapy can replace missing or defective copies of a nucleic acid, and/or restore or impart a new function to overcome a disease.

In one embodiment, the disclosed method of gene therapy is somatic gene therapy and thus applied to the patient undergoing therapy. In one embodiment, the disclosed method of gene therapy is germ line gene therapy and thus not limited to the patient undergoing therapy, being capable of transmission to offspring of the patient. In one embodiment, the disclosed gene therapy methods comprise delivery of a single gene or multiple genes. Multiple genes may be in a single quantum dot complex, or may be in multiple quantum dot complexes. Multiple quantum dot-nucleic acid complexes may be administered either at the same times or at different times. In embodiments where the nucleic acid in the quantum dot complex is in a linear form, e.g., a linear DNA fragment, when introduced into cells, the linear nucleic acid molecules are ligated end-to-end by intracellular enzymes to form long tandem arrays, which promote integration of the nucleic acid into a chromosome.

In embodiments, the disclosed gene therapy methods can be provided alone, or in combination with additional treatments such as stem cell therapy. In one embodiment, a method for treating retinal, CNS, and cardiovascular diseases is provided by providing the disclosed quantum dot-nucleic acid complexes to the patient to effect gene therapy, along with stem cell therapy as known in the art. The therapies may be provided together or separately. In one embodiment, the disclosed method may be provided as part of a combination therapy additionally comprising, e.g., agents such as immunomodulators, anti-VEGF agents, anti-integrins, anti-inflammatory agents, antibiotics, anti-viral agents, anti-fungal agents, anti-proliferative agents, anti-cancer agents, etc.

In one embodiment, the disclosed quantum dot-nucleic acid complex may be targeted and/or directed to a specific region of the body, e.g., a specific organ, tissue type, and/or cell type, where the targeted location may be the site of a disease or a location affected by a disease. In one embodiment, the quantum dot contains or is provided with a coating to enhance or impart biocompatibility and/or cell selectivity using, e.g., an antibody, receptor, etc. that directs the complex to a desired location, e.g., a tumor site, a specific receptor, etc. In one embodiment, targeting or directing the complex may occur using a selected site to provide access to the desired location. For example, in ocular diseases, the disclosed quantum dot-nucleic acid complex may be injected intravitreally, introduced into the cornea, choroid, retina, etc., provided as a topical formulation, etc., as also described herein.

In one embodiment, the disclosed quantum dot-nucleic acid complex may provide both therapeutic and imaging functions. For example, to evaluate the effect of gene modification in the eye, visual acuity electroretinogram, visual field, OCT, ophthalmoscopy, and/or photography may be employed. In one embodiment, the disclosed quantum dot-nucleic acid complex is imaged by photography and/or optical coherence tomography (OCT) in accessible regions such as the eye and skin, and/or is imaged by magnetic resonance imaging (MRI). The ability to image the disclosed complex, particularly when the complex comprises a targeting moiety, provides diagnostic value. Complex accumulation, concentration, or localization at a specific site or area of the body, e.g., breast, brain, prostate, etc., is indicative that this area exhibits the disease or condition to be treated. The disclosed complex may also be imaged by more routine methods such as microscopy visualizing the complex in samples of tissue, including biopsy tissue samples, or body fluids including but not limited to blood.

In one embodiment, the disclosed quantum dot-nucleic acid complex further contains at least one moiety that binds to a tumor-specific protein marker. In one embodiment, the complex still further contains a reporter molecule, in addition to the binding moiety, e.g., an antibody directed to a tumor marker. Reporter molecules are known in the art and include, but are not limited to, molecules that are fluorescent, luminescent, phosphorescent, etc. In this embodiment the complex is administered systemically to a patient to diagnose a tumor by locating and/or imaging the protein-nucleic acid-tumor binding moiety at a tumor site. For example, following administration of the complex to a patient, o the a blood sample is obtained from the patient and subjected to an immunofluorescence assay and/or examined by fluorescent microscopy to detect and/or measure the amount of the tumor marker in the sample. In one embodiment, the quantum dot of the complex and the reporter molecule, such as a fluorescent dye, of the anti-tumor marker antibody have excitation (ex) and emission (em) maxima at different wavelengths, and the sample is examined at multiple wavelengths. The determination of binding by both the complex and anti-tumor marker antibody in the assay provides a more definitive determination that the tumor marker, and thus the tumor, is present in the patient. In one embodiment, the reporter molecule of the anti-tumor marker antibody has emission maxima at the green wavelengths of light. In one embodiment, the specificity of the complex for a tumor is increased by associating multiple tumor marker-binding proteins to the complex. This embodiment provides enhanced opportunities for early detection of a tumor, and prior to tumor metastasis.

The following disclosure demonstrates use in various therapies. In one embodiment, a method for inducing a mammalian cell to produce a recombinant protein is provided. In this embodiment, the disclosed quantum dot-nucleic acid encoding the recombinant protein is provided to a patient. In one embodiment, a method for anemia therapy in a patient is provided. In this embodiment, the disclosed quantum dot-nucleic acid encoding an angiogenic agent, e.g., erythropoietin, is provided to a patient, thereby providing therapy for anemia in the patient. In one embodiment, a method for vasospasm therapy in a patient is provided. In this embodiment, the disclosed quantum dot-nucleic acid encoding inducible nitric oxide synthase (iNOS) is provided to a patient, thereby providing therapy for vasospasm in the patient. In one embodiment, a method for improving cell survival in a patient is provided. In this embodiment, the disclosed quantum dot-nucleic acid encoding a heat shock protein is provided to a patient, therapy providing therapy for increased cell survival. In one embodiment, a method for decreasing incidence of a restenosis of a blood vessel, following a procedure that enlarges the blood vessel, is provided. In this embodiment, the disclosed quantum dot-nucleic acid encoding a heat shock protein is provided to a patient, thereby decreasing incidence of a restenosis in the patient. In one embodiment, a method for increasing growth from a hair follicle in a scalp of a patient is provided. In this embodiment, the disclosed quantum dot-nucleic acid encoding a telomerase or an immunosuppressive protein is provided to a patient, thereby increasing hair growth from a hair follicle. In one embodiment, a method of inducing expression of an enzyme with antioxidant activity in a cell is provided. In this embodiment, the quantum dot-nucleic acid encoding the enzyme is provided to a patient, thereby inducing expression of the enzyme with antioxidant activity in a cell. In one embodiment, a method of cystic fibrosis therapy is provided. In this embodiment, the disclosed quantum dot-nucleic acid encoding Cystic Fibrosis Transmembrane Conductance Regulator (CFTR) is provided, thereby providing therapy for cystic fibrosis in the patient. In one embodiment, a method for treating an X-linked agammaglobulinemia in a patient is provided. In this embodiment, the disclosed quantum dot-nucleic acid encoding a Bruton's tyrosine kinase is provided to a patient, thereby providing therapy for an X-linked agammaglobulinemia in the patient. In one embodiment, a method of therapy for an adenosine deaminase severe combined immunodeficiency (ADA SCID) in a patient is provided. In this embodiment, the disclosed quantum dot-nucleic acid complex encoding an ADA is provided to a patient, thereby providing ADA SCID therapy in the patient. In one embodiment, a method of therapy for hemophilia B in a patient is provided. In this embodiment, the disclosed quantum dot-nucleic acid encoding Factor IX is provided to a patient, thereby providing therapy for hemophilia B. In one embodiment, a method of therapy for spinal muscular atrophy in a patient is provided. In this embodiment, the disclosed quantum dot-nucleic acid complex encoding SMN-1 is provided to a patient, thereby providing therapy for spinal muscular atrophy in the patient. In one embodiment, a method for providing therapy for exudative age related macular degeneration (AMD) in a patient is provided. In this embodiment, the disclosed quantum dot-nucleic acid encoding an anti-VEGF protein is provided, thereby providing therapy to the patient with exudative AMD. In one embodiment, the anti-VEGF protein is sFlt-1, which is a naturally occurring protein antagonist of VEGF. In one embodiment, a method of therapy for choriodemia in a patient is provided. In this embodiment, the quantum dot-nucleic acid complex encoding Rab-Escort Protein (REP-1) is provided to the patient, thereby providing therapy for choriodemia in the patient. In one embodiment, a method of therapy for Leber's congenital amaurosis (LCA) in a patient is provided. In this embodiment, the quantum dot-nucleic acid encoding RPE65 is provided to the patient, thereby providing therapy for Leber's congenital amaurosis in the patient. RPE65 is an RPE-specific 65-kDA protein involved in conversion of all-trans retinol to 11-cis retinal during phototransduction, and has been implicated as a genetic defect in LCA. In one embodiment, a method of therapy for retinitis pigmentosa in a patient is provided. In this embodiment, the quantum dot-nucleic acid encoding MERTK is provided to the patient, thereby providing therapy for retinitis pigmentosa in the patient. In one embodiment, a method of therapy for Stargardt's syndrome in a patient is provided. In this embodiment, quantum dot-nucleic acid encoding ABC4 is provided to a patient, thereby providing therapy for Stargardt's syndrome in the patient. The ABCA4 gene produces a protein involved in energy transport to and from photoreceptor cells in the retina. In one embodiment, a method of therapy for Usher's syndrome (1B) in a patient is provided. In this embodiment, the quantum dot-nucleic acid encoding MY07A is provided to a patient, thereby providing therapy for Usher's syndrome (1B) in the patient. In one embodiment, a method of therapy for advanced and/or metastatic pancreatic cancer in a patient is provided. In this embodiment, the quantum dot-nucleic acid encoding two genes, somatostatin receptor subtype 2 (sst2) and deoxycitidine kinase uridylmonophosphate kinase (dck::umk), which exhibit complementary therapeutic effects, is provided to the patient, thereby providing therapy for advanced and/or metastatic pancreatic cancer in the patient. Both genes induce an antitumor bystander effect and render gemcitabine treatment more efficient.

In embodiments, other ocular pathological conditions as well as additional therapeutic nucleic acids may be provided, some of which were previously described. Examples include, but are not limited to, retinitis pigmentosa, color blindness, wet and dry ARMD, diabetic retinopathy, corneal dystrophies, Meesman syndrome, Fuchs syndrome, granular and macular corneal dystrophies, keratoconous, Sejorgen's syndrome, inherited glaucoma, retinohyaloidopathies, congenital cataract, Marfan syndrome, choridermia x-linked retinoschisis, achromatopsia, etc.

The administration site, location, and/or method of the disclosed quantum dot-nucleic acid complex is not limited. In one embodiment, the disclosed quantum dot-nucleic acid complex may be injected into a vein or artery. In one embodiment, the disclosed quantum dot-nucleic acid complex may be introduced into the cerebrospinal fluid, ventricles, CNS, spinal cord, etc. for therapy of numerous CNS diseases such as Alzheimer's disease, Parkinson's disease, multiple sclerosis, etc. The disclosed method may be used as therapy for patients with spinal muscular dystrophy, muscular dystrophy, diseases affecting myeloid cells, chronic lymphocytic leukemia, multiple myeloma, malignant tumors, melanomas, cancers of various organs including breast, intestine, prostate, CNS, glioblastoma, sarcoma, etc. In addition, the present methods can be used to provide therapy for cystic fibrosis, hemophilia, and sickle cell disease.

In one embodiment, the disclosed quantum dot-nucleic acid complex additionally contains a magnetic or paramagnetic nanoparticle that facilitates introduction of the complex into a cell. In one embodiment, the complex comprises a quantum dot conjugated with a targeting moiety and a biomolecule, such as a gene, DNA, RNA, RNAi, sRNA, plasmid, etc., and a magnetic or paramagnetic nanoparticle also conjugated with the targeting moiety. In embodiments, the targeting moiety is an antibody or a ligand for a receptor.

In one embodiment, a method is provided for introducing the described complex into a desired cell, and thus for introducing the biomolecule, such as a gene for stimulating or silencing cell or tumor cell function. In this embodiment the complex is administered, either systemically or locally, to reach a desired cell. An energy source is then applied, e.g., an alternating magnetic field, electromagnetic radiation, etc., causing a temperature increase in the magnetic or paramagnetic nanoparticle. This temperature increase perturbs the cell membrane of the desired cell, and thus provides or enhances access to the cell at the site of the perturbation, e.g., ranging from an altered membrane conformation to a "hole". Perturbation of the cellular membrane provides enhanced access into the cellular membrane and cytoplasm of the cell. Perturbation of the nuclear membrane provides enhanced access into the nuclear membrane and nucleoplasm of the cell.

Following access of the complex, or at least the nanoparticle containing the biomolecule, into the cell, the biomolecule provides the desired cellular effect. That is, the biomolecule is readily accessible to the cellular cytoplasm or nucleus.

In one embodiment, the quantum dot conjugated with the biomolecule may be coated with a thermosensitive polymer. Thermosensitive polymers are known in the art and include, but are not limited to, chitosan, (poly)ethylene glycol (PEG), etc. Application of an external energy source results in a slight increase in temperature, e.g., to about 39° C. to about 43° C. in one embodiment, to about 40° C. to about 42° C. in another embodiment. This slight temperature increase facilitates release of the biomolecule from the thermosensitive nanoparticles or quantum dot.

In general, the size of the quantum dot defines the wavelength of light that is absorbed by it and, similarly, the wavelength that can be emitted by it which is always longer than that absorbed. For example, a quantum dot with a size of about 200 nm-500 nm dot absorbs a longer wavelength of light than a quantum dot with a size of about 10 nm-50 nm. As a result, the wavelength that is emitted by larger quantum dots will have a larger wavelength (carry less energy, or a shift toward the red), than those wavelengths emitted by smaller quantum dots (carry more energy, or a shift toward the blue). Therefore using different sized quantum dots, one can not only selectively stimulate the specific membrane ion channel or cells, but also make them visible differently due to their different emission of wavelengths of light.

This permits one to selectively activate cells, i.e., turn certain cells on or off, without affecting the other cells. Similarly, such cells selectively activated or turned on can also be coded with one or more different antibody, gene, biomolecule, etc. Such size tunable parameters apply equally to nanowires or nanotubes in addition to quantum dots, and can be used in addition in spectroscopy.

In one embodiment, the complex comprises quantum dots that have two different sizes. Typically, the size of the quantum dots range from about 3 nm to about 50 nm, and the size of the magnetic or paramagnetic nanoparticle ranges from about 70 nm to about 200 nm. In this embodiment, and by way of illustration only, one size of quantum dot is about 10 nm and the other size of quantum dot is about 25 nm. The sizes of the quantum dots are selected such that only one of the two sizes of quantum dot nanoparticles, and not the other size quantum dot nanoparticle, is susceptible to the external energy and increases in temperature, as described above for the magnetic or paramagnetic nanoparticle.

In one embodiment, the disclosed complex is activated by a light source that is implanted in the patient. This embodiment finds particular beneficial use for methods in which the quantum dot-nanoparticle is, or is likely to be, located at a body region or site that is less readily accessible or inaccessible to an external energy source, e.g. brain, spinal cord, etc. In one embodiment, an LED light source with a rechargeable battery is implanted in the patient. The LED provides a light pulse that activates the disclosed complex. In one embodiment, the light is transmitted by a fiber optic or a flexible silicone tube to a desired area(s). In this embodiment, the disclosed complex need not necessarily be localized to the desired site for treatment, but the localized production of light causes activation of the complex at a desired site to treat the condition. The implanted LED/battery functions similar to an implanted cardiac pacemaker. It controllable parameters, e.g., pulse frequency, can be controlled before or after implantation. In embodiments, the implanted LED/battery is used with the disclosed quantum dot-nucleic acid complex for therapy of patients with Parkinson's disease, epilepsy, spinal cord injury, and neurological diseases affecting an action potential.

In one embodiment, a method for transferring IGF-I to a cirrhotic liver using the disclosed quantum dot-nucleic acid encoding IGF-I where IGF-I is under control of a liver-specific promoter, is provided. Results show improved liver function and reduced liver fibrosis. As used herein, IGF-I is used interchangeably with insulin-like growth factor I and somatomedin C and relates to a family of polypeptides characterized by showing insulin-like effects and insulin-like structure, sharing nearly 50% of amino acid homology with insulin.

In one embodiment, a method of expressing GLP-1 protein using the disclosed quantum dot-nucleic acid complex encoding GLP-1 or a GLP-1 analog provides therapy for type II diabetes. A GLP-1 analog, also encompassed, is defined as a molecule having a modification including one or more amino acid substitutions, deletions, inversions, or additions when compared with GLP-1. GLP-1 analogs known in the art include, e.g., GLP-1(7-34) and GLP-1(7-35), GLP-1(7-36), Val$^8$-GLP-1(7-37), Gln$^8$-GLP-1(7-37), D-Gln$^8$-GLP-1(7-37), Thr$^{16}$-Lys$^{18}$-GLP-1(7-37), and Lys$^{18}$-GLP-1(7-37), disclosed in U.S. Pat. Nos. 5,118,666, 5,545,618, and 6,583,111. These compounds are the biologically processed forms of GLP-1 having insulinotropic properties.

In one embodiment, the disease for which the quantum dot-nucleic acid complex is provided is characterized by dysregulation of the immune system. In this embodiment, the nucleic acid encodes a cytokine such as human interferon α2b (hINFα) for therapy.

In one embodiment, using the disclosed methods, a tumor suppressor gene or genes is provided to a patient in need thereof, such as a cancer patient. A tumor suppressor gene as used herein means a nucleotide sequence that may inhibit a tumor phenotype depending on its expression in the cell or may induce apoptosis. Many tumors lack functional tumor suppressor genes that encode proteins that can arrest tumor growth and promote tumor cell apoptosis. For example, the p53 protein arrests the cell cycle following DNA damage and is also involved in apoptosis. Efficient delivery and expression of the wild-type p53 gene cause regression of established human tumors, prevent growth of human cancer cells in culture, and renders malignant cells from human biopsies non-tumorigenic in nude mice. The p53 gene has been combined with standard therapies such as chemotherapy and radiotherapy with positive effect. In one embodiment, a method of therapy for cancer in a patient is provided. In this embodiment, the quantum dot-nucleic acid encoding p53 is provided to a patient, thereby providing therapy to the patient. Besides the p53 gene, other tumor suppressor genes include APC gene, DPC-4/Smad4 gene, BRCA-1 gene, BRCA-2 gene, WT-1 gene, retinoblastoma gene (Lee et al., Nature, 329: 642 (1987)), MMAC-1 gene, adenomatouspolyposis coil protein, deleted in colorectal cancer (DCC) gene, MMSC-2 gene, NF-1 gene, nasopharyngeal carcinoma tumor suppressor gene that maps at chromosome 3p21.3, MTS1 gene, CDK4 gene, NF-1 gene, NF-2 gene and/or VHL gene.

Other therapeutic genes useful for the disclosed method include those that encode enzymes, blood derivatives, hormones, lymphokines such as interleukins, interferons, tumor necrosis factor, etc., growth factors, neurotransmitters or their precursors or synthetic enzymes, trophic factors namely BDNF, CNTF, NGF, IGF, GMF, αFGF, βFGF, NT3, NT5, HARP/pleiotrophin, etc., apolipoproteins such as ApoAI, ApoAIV, ApoE, etc., dystrophin or a minidystrophin, the CFTR protein associated with cystic fibrosis, intrabodies, tumor-suppressing genes such as p53, Rb, Rap1A, DCC, k-rev, etc., genes encoding coagulation factors such as factors VII, VIII, IX, genes participating in DNA repair, suicide genes defined as genes whose products cause cell death, e.g., thymidine kinase (HS-TK), cytosine deaminase, etc., pro-apoptic genes, prodrug converting genes defined as genes encoding enzymes that convert prodrugs to drugs, and anti-angiogenic genes or alternatively, genes such as VEGF that promote angiogenesis.

The nucleic acid portion of the quantum dot-nucleic acid complex can also be used in gene silencing. Such gene silencing may be useful in therapy to switch off aberrant gene expression or studies to create single or genetic knockout models. Such nucleic acid is typically provided in the form of siRNAs. For example, RNAi molecules including siRNAs can be used to knock down DMPK with multiple CUG repeats in muscle cells for myotonic dystrophy therapy. In other examples, plasmids expressing shRNA that reduce the mutant Huntington gene (htt) responsible for Huntington's disease can be delivered. Other target genes include BACE-1 for the therapy of Alzheimer's disease. Some cancer genes may also be targeted with siRNA or shRNAs, such as ras, c-myc and VEGFR-2. Brain targeted siRNA may be useful in silencing BACE-1 in Alzheimer's disease, silencing of α-synuclein in Parkinson's disease, silencing of htt in Huntingdon's disease, and silencing of neuronal caspase-3 used in therapy of stroke to reduce ischemic damage.

In one embodiment, the nucleic acid is an RNA interference (RNAi), small interfering RNA or short interfering RNA (siRNA), short hairpin RNA (shRNA) molecule, or miRNA which is a RNA duplex of nucleotides targeted to a nucleic acid sequence of interest, e.g. huntingtin. As used herein, siRNA is a generic term that encompasses the subset of shRNAs and miRNAs. An RNA duplex refers to the structure formed by the complementary pairing between two regions of a RNA molecule. siRNA is targeted to a gene in that the nucleotide sequence of the duplex portion of the siRNA is complementary to a nucleotide sequence of the targeted gene. In embodiments, siRNAs are targeted to the sequence encoding ataxin-1 or huntingtin. In embodiments, the length of the duplex of siRNAs is less than 30 base pairs. In embodiments, the duplex can be 29, 28, 27, 26, 25, 24, 23, 22, 21, 20, 19, 18, 17, 16, 15, 14, 13, 12, 11 or 10 base pairs in length. In embodiments, the length of the duplex is 19 to 25 base pairs in length. In embodiment, the length of the duplex is 19 or 21 base pairs in length. The RNA duplex portion of the siRNA can be part of a hairpin structure. In addition to the duplex portion, the hairpin structure may contain a loop portion positioned between the two sequences that form the duplex. The loop can vary in length. In embodiments the loop is 5, 6, 7, 8, 9, 10, 11, 12, 13, 14, 15, 16, 17, 18, 19, 20, 21, 22, 23, 24 or 25 nucleotides in length. In embodiments, the loop is 18 nucleotides in length. The hairpin structure can also contain 3' and/or 5' overhang portions. In embodiments, the overhang is a 3' and/or a 5' overhang 0, 1, 2, 3, 4 or 5 nucleotides in length. In one embodiment, the various forms of RNA such as microRNA, RNA interference, RNAi, and siRNA are designed to match the RNA copied from a defective gene, thereby inhibiting or diminishing production of the abnormal protein product of that gene.

In some embodiments, it may be useful to assess, monitor, track, evaluate location, evaluate stability, etc. of the quantum dots conjugated or otherwise associated with a moiety as previously described. In these embodiments, the quantum dots are tagged with a recognition moiety to provide a signal, and may themselves be conjugated to another biologically active moiety, e.g., DNA, RNA, peptide, protein, antibody, enzyme, receptor, etc., as known to one skilled in the art. Tagging may be effected via a covalent bond with a amide, thiol, hydroxyl, carbonyl, sulfo, or other such group on the biologically active moiety, as well known to one skilled in the art.

While each solar cell particle is oriented, the plurality of particles provided in the body are not uniformly directionally oriented, nor do they require a backing layer to maintain orientation or position. They have a positive-negative (P-N) junction diode and may be constructed as either negative-intrinsic-positive (NIP) or positive-intrinsic-negative (PIN), as known to one skilled in the art.

As an example, p-type silicon wafers, and doped p-type silicon wafers to form n-type silicon wafers, are contacted to form a p-n junction. Electrons diffuse from the region of high electron concentration, the n-type side of the junction, into the region of low electron concentration, the p-type side of the junction. When the electrons diffuse across the p-n junction, they recombine with an electron deficiency (holes) on the p-type side. This diffusion of carriers does not happen indefinitely however, because of the electric field created by the imbalance of charge immediately either side of the junction which this diffusion creates. Electrons from donor atoms on the n-type side of the junction cross into the p-type side, leaving behind the (extra) positively charged nuclei of the group 15 (V) donor atoms such as phosphorous or arsenic, leaving an excess of positive charge on the n-type side of the junction. At the same time, these electrons are filling holes on the p-type side of the junction and are becoming involved in covalent bonds around the group 13

(III) acceptor atoms such as aluminum or gallium, making an excess of negative charge on the p-type side of the junction. This imbalance of charge across the p-n junction sets up an electric field which opposes further diffusion of charge carriers across the junction. The region where electrons have diffused across the junction is called the depletion region or the space charge region because it no longer contains any mobile charge carriers. The electric field which is set up across the p-n junction creates a diode, allowing current to flow in only one direction across the junction. Electrons may pass from the n-type side into the p-type side, and holes may pass from the p-type side to the n-type side. Because the sign of the charge on electrons and holes is opposite, current flows in only one direction. Once the electron-hole pair has been created by the absorption of a photon, the electron and hole are both free to move off independently within a silicon lattice. If they are created within a minority carrier diffusion length of the junction, then, depending on which side of the junction the electron-hole pair is created, the electric field at the junction will either sweep the electron to the n-type side, or the hole to the p-type side.

One embodiment of the invention uses nanocrystals of semiconductor material referred to as quantum dots (Evident Technologies, Troy N.Y.; Oceano NanoTech, Springdale Ak.). Nanocrystal solar cells are solar cells based on a substrate with a coating of nanocrystal. The nanocrystals are typically based on silicon, CdTe or CIGS and the substrates are generally silicon or various organic conductors. Quantum dot solar cells are a variant of this approach. These have a composition and size that provides quantum properties between that of single molecules and bulk materials, and are tunable to absorb light over the spectrum from visible to infrared energies. Their dimensions are measured in nanometers, e.g., diameter between about 1 nm to about 100 nm. When combined with organic semiconductors selected to have the desired activation properties, they result in particles with selectable features. The particles can also have passive iron oxide coatings with or without polyethylene glycol coatings or positive charge coatings as commercially provided. Quantum dot solar cells take advantage of quantum mechanical effects to extract further performance.

Nanocrystals are semiconductors with tunable bandgaps. The quantum dot nanocrystal absorption spectrum appears as a series of overlapping peaks that get larger at shorter wavelengths. Because of their discrete electron energy levels, each peak corresponds to an energy transition between discrete electron-hole (exciton) energy levels. The quantum dots do not absorb light that has a wavelength longer than that of the first exciton peak, also referred to as the absorption onset. Like other optical and electronic properties, the wavelength of the first exciton peak, and all subsequent peaks, is a function of the composition and size of the quantum dot. Smaller dots result in a first exciton peak at shorter wavelengths.

The quantum dots may be provided as a core, with a shell or coating of one or more atomic layers of an inorganic wide band semiconductor. This increases quantum yield and reduces nonradiative recombination, resulting in brighter emission provided that the shell is of a different semiconductor material with a wider bandgap than the core semiconductor material. The higher quantum yield is due to changes in the surface chemistry of the core quantum dot. The surface of nanocrystals that lack a shell has both free (unbonded) electrons, in addition to crystal defects. Both of these characteristics tend to reduce quantum yield by permitting nonradiative electron energy transitions at the surface. A shell reduces opportunities for nonradiative transitions by giving conduction band electrons an increased probability of directly relaxing to the valence band. The shell also neutralizes the effects of many types of surface defects.

The quantum dots may respond to various wave lengths of electromagnetic radiation, i.e., visible, invisible, ultrasound, microwaves. The quantum dots respond by emitting an electrical potential or fluoresce when exposed to electromagnetic radiation. The quantum dots may be made, or self-assembled, from CdSe and a shell of zinc gallium arsenide, indium gallium selenide, or cadmium telluride. Luminescent semiconductor quantum dots such as zinc sulfide-capped cadmium selenide may be covalently coupled to biomolecules for use in ultrasensitive biological detection. These nanometer-sized conjugates are water-soluble and biocompatible.

Quantum dots, organic quantum dots or solar cells, may be made from organic molecules such as organic nanocrystal solar cells, polymers, fullerenes, etc. Quantum dots may be coated with organic molecules, biocompatible proteins, peptides, phospholipids, or biotargeted molecules etc., or covalently attached to polyethylene glycol polymers (i.e., they may be PEGylated) to last longer. These quantum dots, or devices containing quantum dots are amenable to large scale production. They may be built from thin films, polymers of organic semiconductors. These devices differ from inorganic semiconductor solar cells in that they do not rely on the large built-in electric field of a PN junction to separate the electrons and holes created when photons are absorbed. The active region of an organic device consists of two materials, one which acts as an electron donor and the other as an acceptor. The short excitation diffusion lengths of most polymer systems tend to limit the efficiency of such devices. However, quantum dots can be used for cell membrane stimulation.

The quantum dots can be made to respond to various wavelengths of light (visible and invisible). In one embodiment they are coated with organic molecules. In one embodiment, they are completely organic. In one embodiment, they are PEGylated to last longer. In one embodiment, they are coated to be attracted to certain receptors or stay only on the cell surface.

Bioelectrical signals exist in all cells and play an important role in allowing the cells to communicate with each other. Quantum dots can facilitate these signal transmission between the cells, such as through cell membranes and their membrane potentials, thereby maintaining normal function in the tissue which include cell survival and growth, individually or collectively. Quantum dots can enhance regeneration of the cells. Quantum dots can enhance neural axons and enhance the wound healing process.

Cell activity relates to depolarization and re-polarization of the cell membrane. Quantum dots can regulate polarization and depolarization and thus enhance the action potential of the membrane. Lack of cell activity leads to cell atrophy. Similarly, loss of the cell membrane potential causes cell degeneration and atrophy. The therapeutic effects of quantum dots are achieved by the effects that quantum dots exert on membrane potential when stimulated, e.g. light, photoelectrical, ultrasound, etc. In the eye and in the nervous system, quantum dots can be stimulated (e.g., through the cornea, sclera or skull etc. for the brain, spinal cord, and nerves), thus enhancing or maintaining the cell membrane potential (e.g., nerve cell, glial cells, astrocytes, etc.). This process preserves the function of such cells (nerve cells, glial cells, astrocytes, etc.) by maintaining their membrane potentials, thus maintaining cell viability and function.

In one embodiment, the method and concept is applied to the eye. In one embodiment, the method and concept is applied to the brain and spinal cord nerve cells and axons. In this embodiment, the method is used to enhance or stimulate regrowth of nerve cells, axons, and/or other brain and spinal cord tissue.

In one embodiment, the effects of quantum dots on the cells can be enhanced by combining quantum dots with growth factors. Such growth factors are known to one skilled in the art, and include but are not limited to nerve growth factors, glial growth factors, placenta growth factor, etc. In one embodiment the effects of quantum dots on the cells can be enhanced by administering and/or regulating quantum dots essentially simultaneously with certain pharmaceuticals or agents, including but not limited to TAXOL®, carbonic anhydrase inhibitors, etc. Quantum dots, when activated by light, enhance drug penetration through the cell membrane. This can be used therapeutically in combination with many medications which may not penetrate the cell membrane easily because of their chemical structures. However, this concept can be used also in conjunction with antibiotics, antifungal agents, etc. to kill the organism that caused skin or mucosa ulcers resisting therapy.

The treatment can be done easily by topically applying quantum dots along with the appropriate medication and using light to activate the quantum dots. The method of delivery to the eye may be by injection, eye drops, ointments, sprays or other applications to treat an optic nerve. The method of delivery to the brain may be by injection of the quantum dots into cerebrospinal fluid, brain ventricles, intra-ocularly, or administration by nasal sprays or drops. The method of delivery to the skin or mucosa, e.g., nasal mucosa, is by spraying. Most of these applications avoid possible systemic side effects. The size of the particles allows them to easily diffuse into tissues. For neural applications other than the eye, quantum dots, either conjugated or associated with a drug, and/or administered without a drug or other agent, are administered by any route of delivery including but not limited to local, systemic, injection in the CNS, by nasal routes, e.g., spray, drops, to regulate the nasal olfactory nerve, or localized injection in the vicinity of the peripheral nerves or ganglions, etc.

In one embodiment, the inventive method is used in a patient with a neurological disorder. While described in detail for use in a patient with epilepsy, which is a common neurological disorder requiring treatment, the inventive method is not so limited and encompasses any neurological disorder of the central and/or peripheral nervous system. Epilepsy is thus used an exemplary but non-limiting embodiment of use of the method.

Epilepsy is a chronic condition that transiently affects about 50 million individuals. It is not a single disorder, but instead is a group of syndromes with vastly divergent symptoms. Its unifying and diagnostic feature is episodic abnormal electrical activity in the brain that results in seizures. These seizures are transient, recurrent, and unprovoked; signs and/or symptoms of abnormal, excessive, or synchronous neuronal activity in the brain. All seizures involve loss of consciousness; types of seizures are characterized according to their effect on the body. These include absence (petit mal), myoclonic, clonic, tonic, tonic-clonic (grand mal), and atonic seizures.

Some forms of epilepsy are confined to particular stages of childhood. In children, epilepsy may result from genetic, congenital, and/or developmental abnormalities. In adults over 40, it may result from tumors. At any age, it may result from head trauma and central nervous system infections. Post-traumatic epilepsy (PTE) is a form of epilepsy that results from brain damage caused by physical trauma to the brain: traumatic brain injury (TBI). An individual with PTE suffers repeated post-traumatic seizures (PTS) more than a week after the initial injury. PTE can also occur after infectious diseases involving the CNS or peripheral nerves.

Epilepsy is usually controlled, but not cured, with medication, although surgery is sometimes needed. Therapeutic agents include (a) sodium channel blockers (voltage dependent), (b) calcium channel blockers (T-type), (c) potentiators of GABA (inhibitory), and (d) those that decrease excitatory transmission (glutaminic).

Some medication, administered daily, may prevent seizures altogether or reduce their frequency. Such medications, termed anticonvulsant drugs or antiepileptic drugs (AEDs), include valproate semisodium (Depakote, Epival), valproic acid (Depakene, Convulex), vigabatrin (Sabril), and zonisamide (Zonegram). A problem is that all have idiosyncratic and non-dose-dependent side effects. Thus, one cannot predict which patients on a therapeutic, regimen will exhibit side effects or at what dose.

Some medications are commonly used to abort an active seizure or to interrupt a seizure flurry. These include, diazepam (Valium) and lorazepam (Ativan) Drugs used only in the treatment of refractory status epilepticus include paraldehyde (Paral), midazolam (Versed), and pentobarbital (Nembutal).

Bromides, the first of the effective anticonvulsant pure compounds, are no longer used in humans due to their toxicity and low efficacy.

Palliative surgery for epilepsy is intended to reduce seizure frequency or severity. For example, a callosotomy or commissurotomy is performed to prevent seizures from generalizing, i.e., from being transmitted to the entire brain, which results in loss of consciousness Vagus nerve stimulation (VNS) controls seizures with an implanted electrical device, similar in size, shape, and implant location to a pacemaker. The implanted VNS device connects to the vagus nerve in the neck and is set to emit electronic pulses to stimulate the vagus nerve at pre-set intervals and milliamp levels. About 50% of individuals with an implanted VNS device showed significantly reduced seizure frequency.

The Responsive Neurostimulator System (tRNS), in clinical study prior to regulatory approval, is a device implanted under the scalp with leads implanted either on the brain surface or in the brain close to the area where the seizures are believed to start. At the outset of a seizure, small amounts of electrical stimulation are delivered to the brain to suppress the seizure. The RNS system differs from the VNS: the RNS system is patient responsive in that it directly stimulates the brain, whereas the VNS system provides physician-determined pre-set pulses at predetermined intervals. The RNS system is designed to respond to detected signs that a seizure is about to begin and can record events and allow customized response patterns that may provide a greater degree of seizure control.

One class of therapeutic agents for treating epilepsy are the carbonic anhydrase inhibitors, but all have undesirable side effects.

Acetazolamide (Acz), a known inhibitor of carbonic anhydrase, is one such agent. It prevents hypoxic pulmonary vasoconstriction (HPV) and thus is also used to treat altitude sickness, glaucoma, and benign intracranial hypertension. Acetazolamide, however, affects kidney function because it reduces NaCl and bicarbonate reabsorption in the kidney proximal tubule. The reduction results in a mild diuretic effect, although it is partially compensated by the kidney distal segment and the metabolic acidosis produced by the bicarbonaturia. Methazolamide, also a carbonic anhydrase inhibitor, is longer-acting than acetazolamide with fewer kidney effects. Dorzolamide, a sulfonamide and topical carbonic anhydrase II inhibitor, reduces the elevated intraocular pressure in patients with open-angle glaucoma or ocular hypertension that are insufficiently responsive to beta-blockers. Inhibition of carbonic anhydrase II in the ciliary processes of the eye decreases aqueous humor secretion, presumably by slowing the formation of bicarbonate ions with subsequent reduction in sodium and fluid transport. Topiramate is a weak inhibitor of carbonic anhydrase, particularly subtypes II and IV. It is a sulfamate-substituted monosaccharide that is related to fructose. In is approved in the U.S. as an anticonvulsant to treat epilepsy, migraine headaches, and Lennox-Gastaut syndrome. Its inhibition of carbonic anhydrase may be sufficiently strong to result in clinically significant metabolic acidosis.

Acetazolamide and other calcium-inhibiting sulfonamides increase intracellular pH and relax mesenteric arteries preconstricted with norepinephrine. Calcium inhibitors and/or the intracellular alkalinization activate a calcium-dependent potassium channel, resulting in hyperpolarization of the vascular smooth muscle cell, reduction of voltage-dependent calcium channel activity, decreased intracellular calcium, and vasorelaxation.

Spreading depression (SD) is a pathophysiologic event characterized by depressed EEG activity and a change of the direct current potential as an indicator of a short-lasting cell membrane depolarization. It may be induced by a variety of cortical stimuli, including potassium chloride or glutamate application, and electrical or mechanical stimulation; it also occurs secondary to ischemia. It is accompanied by severe changes in ion homeostasis and water shifts from the extracellular to intracellular space, mirrored by changes of electrical impedance and direct current (DC) potential. The area of depolarization spreads along cortical tissue like a wave, moving away from the initiation site toward the periphery, and propagates with an estimated velocity of 3 μm/min. Electrical measurements from the cortex surface show negative deflection of the DC potential, lasting 1 to 2 minutes, combined with EEG suppression. Under normoxic conditions, SD is not followed by permanent neuronal damage, and the depressed neuronal activity is compensated by increased glucose metabolism and blood flow during the repolarization phase. The cell membrane repolarization requires an enormous metabolic effort and is compensated by increased glucose metabolism and increased blood flow.

Serotonin homeostasis, regulated by serotonin receptor 1A (Htr1a), is required for normal serotonin levels. Htr1a also mediates autoinhibition of serotonin production; excessive serotonin autoinhibition is associated with sporadic autonomic dysregulation and death. Tryptophan, a serotonin precursor, increases serotonin production. Administration of the selective Htr Ia antagonist WAY100635 completely shuts down serotonin-induced neuron impulses, resulting in apnea preceded by bradycardia; both lung function and heart function were affected.

Spreading depression (SD) has been extensively studied and is likely an important mechanism in several human diseases. Cerebral hemodynamics, i.e., cerebral blood volume and water changes, were assessed by high-speed MRI during potassium-induced spreading depression. MRI images, and brain voltage readings, were used to determine apparent diffusion coefficients over time that correlated with potassium flux along the cortex. Acetazolamide treatment resulted in vasodilation and arrested spreading depression.

Diffusion-weighted imaging is highly sensitive to slowing water proton translations early in the ischemic episode, i.e., within minutes. MR imaging measured the ADC of brain water decreases by 30% to 60%, and recent findings suggested significant apparent diffusion slowing (ADC decreases) in stroke results predominantly due to cellular swelling and reflects a shift of relatively faster translating extracellular water protons into a more hindered intracellular environment. It has been shown that when the $Na^4/K^4$ pump is disabled by intraparenchymal ouabain, the ADC decreases. This supports a link between altered ion homeostasis and alteration in ADC. There is a relation between membrane polarization and diffusion as measured by the ADC. Failure of the transmembrane ion pumps and subsequent loss in cell membrane potential is immediately followed by disruption of ion homeostasis. The resulting ionic imbalance causes an osmotically driven flow of water into the cells. MR imaging indicates the subsequent cell swelling with restricted extracellular or intracellular diffusion, and increased extracellular tortuosity, reduces the ADC.

The concept of cell preservation by quantum dots administration and treatment applies to the above these diseases and reduces degeneration of all brain cells (nerve cells, glial cells, etc.).

Quantum dots are useful in providing repeated electric pulses either to the brain, spinal cord, or isolated nerve cells that are involved with various neural disorders. In disorders involving these regions low level brain, spinal cord, etc. neural pulses are not passing through for one reason or another, e.g., synapses, scar, misdirection, etc., and are released either as a giant pulse or can circuit back and forth until the membrane potential is completely exhausted. Therefore a pulsed stimulation by an external source, such as light or electric pulses applied to the brain, ventricles, spinal cord. cerebrospinal fluid, having quantum dots would eliminate an avalanche of the pulses in posttraumatic epilepsy, restless leg syndrome, spinal cord epilepsy, etc. A version of this concept could be potentially used to modify brain waves needed for sound sleep, alleviation of depression, etc. Stimulation of the olfactory nerve can enhance neuronal regeneration in the brain in aging adults or in Alzheimer's disease or slow its progression.

A physician may select specific properties and emission frequencies to selectively regulate polarization in specific sites and for specific results. Thus, the particles are tunable to provide desired properties; for example, they may be size specific, current specific, patient specific, disease specific, activation specific, site specific, etc.

As one example, particles provided throughout the retinal layers may be selectively regulated to normalize polarization and/or reduce or prevent repolarization, depolarization, and/or hyperpolarization. As another example, selected particles may be administered to selected sites and selectively regulated (e.g., temporally, spatially, activationally, etc.) to result in different effects to fine-tune a desired outcome. More specifically, a patient's progress may be monitored after a slight regulation and, if warranted, further regulation may be administered until a desired outcome is obtained. For example, a patient with muscle tremors may be treated with the inventive method for a duration, extent, activation energy, etc. to selectively repolarize striated muscle cells until a desired effect is reached.

In embodiments, the disclosed complex comprises nanoparticles other than quantum dots; these include nanowires, nanorods, etc. In embodiments containing a biomolecule, the complex comprises at least a first nanoparticle and a second nanoparticle where the first and the second nanoparticles absorbs energy at different wavelengths, and thus are activated by different energy wavelengths, e.g., light. This embodiment permits control of the activity of the complex, e.g., selective activation using different energy wavelengths, providing further control of the physiological function of excitable cells. In embodiments comprising a biomolecule that targets the complex to a specific location, tissue, cell, etc., the complex comprising multiply excited particles can be used for diagnostic identification. For example, it can be used to identify a specific cell type.

In one embodiment, the particles are mixed into or with a biocompatible fluid. In another embodiment, the particles are in the form of beads or spheres. In another embodiment, the particles are provided as a film. In another embodiment, the particles are drawn and provided as fibers. In any of these embodiments, the particles are provided to a patient by injection to other minimally invasive techniques known to one skilled in the art.

Upon administration, the particles are disseminated and/or located intracellularly (within a cell), intercellularly (between cells), or both intracellularly and intercellularly. They may be administered in a number of ways. With respect to the eye, they may be injected through the retina, under the retina superiorly, over the fovea, through the outer plexiform layer down to the fovea, into the vitreous cavity to diffuse through the retina, etc. The procedure permits particles to be located at any site including the macula, that is, the particles may be directly on the macula, directly on the fovea, etc. distinguishing from procedures requiring electrodes to be located beyond the macula or beyond the fovea so as not to block foveal perfusion. The procedure does not require major invasive surgery and is only minimally invasive, in contrast to procedures that involve surgical implantation of an electrode or photovoltaic apparatus. The procedure locates particles diffusively substantially throughout the eye, or selected regions of the eye, in contrast to procedures in which an electrode or other device is located at a single site. Thus, the site of treatment is expanded with the inventive method. In this way, the particles locate within excitable cells, such as the retina, macula, etc. using an ocular example, and also locate between these excitable cells, and are thus dispersed substantially throughout a region of interest. Particles not located as described are handled by the retinal pigment epithelium.

Continuing to use the eye as a non-limiting example, the particles migrate through spaces of retinal cells and distribute through retinal layers, including the RPE. To even more widely disperse particles throughout the retina, they may be sprayed over the retina. In one embodiment, they may be delivered and distributed throughout the retinal layers by a spraying or jetting technique. In this technique, a pressurized fluid (liquid and/or gas) stream is directed toward a targeted body tissue or site, such as retinal tissue, with sufficient energy such that the fluid stream is capable of penetrating the tissue, e.g., the various retinal layers. In applications, the fluid stream, which may be a biologically compatible gas or liquid, acts as a carrier for the particles. By way of example, the spraying technique has been used in cardiac and intravascular applications for affecting localized drug delivery. The teaching of those applications may be applied to the delivery of the particles to the retina. For example, U.S. Pat. No. 6,641,553 which is expressly incorporated by reference herein, discloses pressurizing a fluid carrier having a drug or agent mixed therewith and jetting the mixture into a target tissue.

It will also be appreciated that other agents may be included in the fluid in addition to the particles. These other agents include, but are not limited to, various molecules, drugs that have stimulatory or inhibitory activity (e.g., protein drugs, antibodies, antibiotics, anti-angiogenic agents, anti-prostaglandins, anti-neoplastic agents, etc.), vectors such as plasmids, viruses, etc. containing genes, oligonucleotides, small interfering RNA (sRNA), micro-RNA (miRNA), etc.

In one embodiment, quantum dots conjugated or otherwise associated with a molecule or biomolecule are delivered to an eye to enhance functional recovery of an at least partially functional retinal cell in a patient in need of such treatment. This embodiment of the method may be in addition to, or in place of, the method of regulating membrane polarity using the introduced quantum dot previously described. The quantum dot-biomolecule conjugate or particle may be provided to a retinal cell cytoplasm or a retinal cell nucleus, with injection or other introduction means into the subretinal space, into the retina itself, into the macula, under the macula, into the vitreous cavity with vitreous fluid present, and/or into the vitreous cavity with vitreous fluid absent. The quantum dots conjugated or otherwise associated with a vector carrying a protein or other molecule capable of modifying genes in retinal cell provides gene therapy. In one embodiment, racking means (e.g., sensors or other signals) associated with the complex are used to monitor location, stability, functionality, etc. of the complex.

In one embodiment the retinal or other cell so modified by the method contains a light-sensitive protein that itself may be excited directly by light of a specific wavelength, or in an alternative embodiment, be excited by light of a different wavelength or produced by the quantum dot (e.g., fluorescence) after the quantum dot is excited upon exposure of light. For example, if the modified genes of the cell produce halorrhodopson, then the quantum dots to which the halorhodopsin-encoding gene were associated can be excited to then activate the halorhodopsin to silence the cell. If the modified genes of the cell produce channelrhodopsin, then the quantum dots to which the channelrhodopsin-encoding genes were associated can enhance an action potential. As known to one skilled in the art, channelrhodopsins, a family of proteins, function as light-gated ion channels in controlling electrical excitability among other functions. As known to one skilled in the art, halorhodopsin is a light-activated chloride-specific ion pump. When quantum dots are combined with channelrhodopsins or halorrhodopsons, quantum dots enhance the effects of these proteins, and result in enhanced cell polarization responsive to light stimulation.

In one embodiment, quantum dots conjugated or otherwise associated with a molecule or biomolecule are delivered to the heart to enhance functional recovery of an at least partially functional heart cell in a patient in need of such treatment.

In one embodiment of monitoring, a video camera receives an image of the external environment that is projected into an eye containing the functional, excitable retinal cell to be treated. For example, after initial administration of the quantum dots to the eye, a camera mounted on or in the eyeglasses records and produces a digitized image of the external environment, which is then transmitted to a small computer mounted on the glasses. The picture can be recreated on an LCD using a diode array. This image, in turn, is projected through the pupil, onto the retina containing quantum dots to stimulate rods and cones. This process may be optionally repeated to determine the extent or degree to excite the quantum dots and/or to achieve the desired cell polarization state by evaluating retinal function, e.g., by electroretinogram or other methods known to one skilled in the art.

In one embodiment, the eye imaging method, e.g., OCT, confocal microscopy, provides a method of tracking the quantum dots in cells, e.g., stable cells such as neurons.

In one embodiment, the treated cells are restored to normal polarization by treatment using the quantum dots; and concomitantly, the cells are treated with a biological moiety conjugated to the quantum dots to relieve, restore, ameliorate, or treat a functional condition of the retinal cell, e.g., a retinal genetic disease. In one embodiment, the biologically active conjugate is biologically active after the quantum dot ceases to be functional. In one embodiment the quantum dot is active after the biologically active conjugate ceases to be functional.

Figure 3:
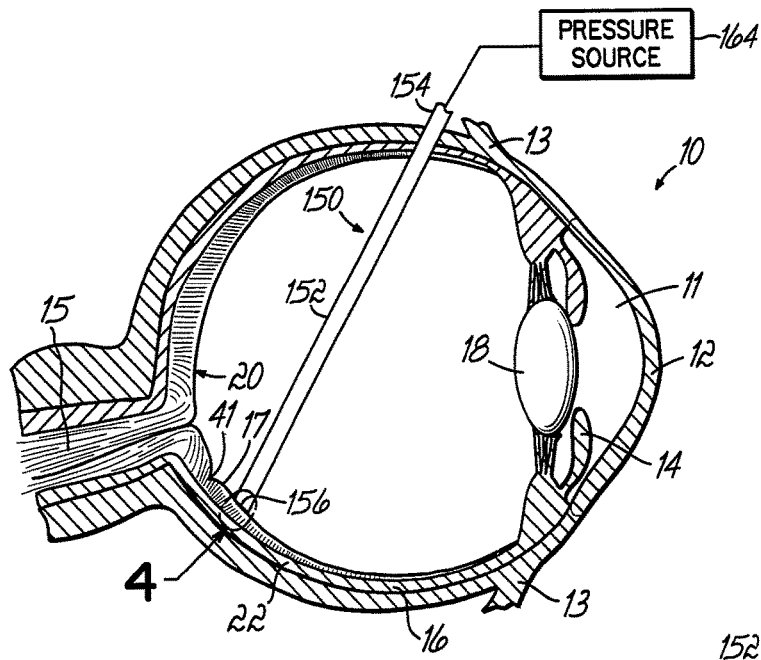
FIG. 3 shows the eye of FIG. 1 with a cannula delivering particles to the retina in accordance with one embodiment of the invention.
Figure 4:
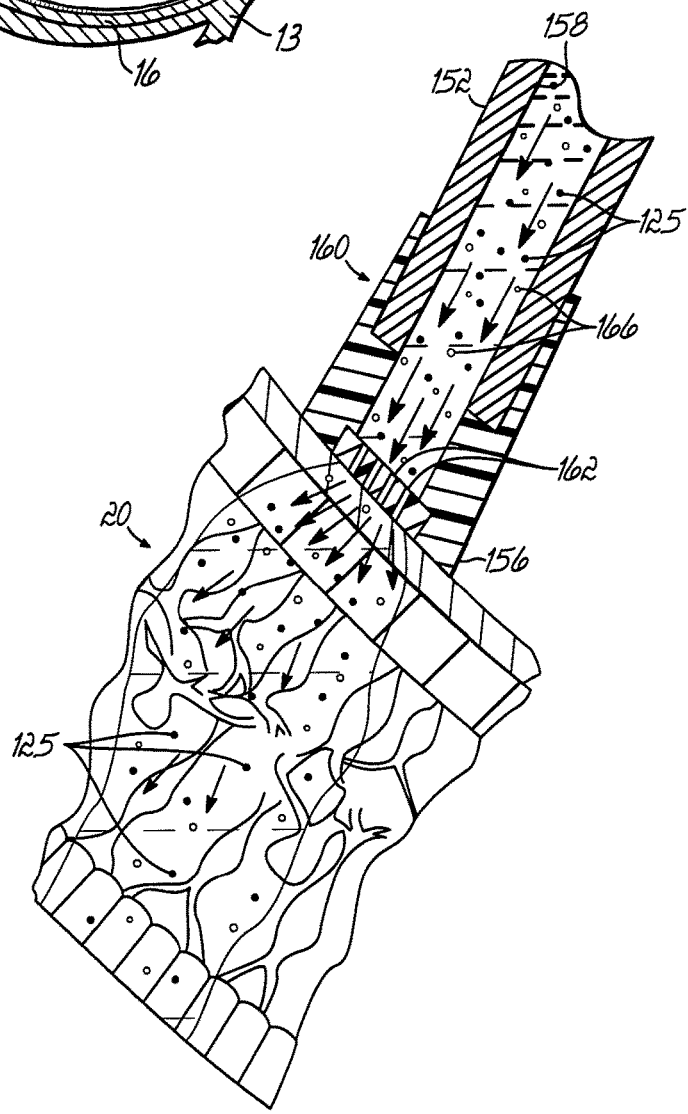
FIG. 4 is an enlarged diagrammatic illustration of the circled area 4 in FIG. 3 showing particles jetting from a cannula and dispersing throughout retinal structures.

As schematically shown in FIGS. 3 and 4, a device 150 for delivering the particles to the retina generally includes an elongated tube or cannula 152 having a proximal end 154 and a distal end 156 and an interior lumen 158 extending between the proximal and distal ends 154, 156. A distal end region 160, which may include a distal end face or a portion of the outer surface of the cannula 152 adjacent the distal end 156, includes a plurality of outlet ports or apertures 162 in fluid communication with the interior lumen 158. The device 150 further includes a pressure control source 164, such as for example a fan or pump, in fluid communication with the lumen 158 and operable for establishing an elevated pressure within the lumen. As known to one skilled in the art, the pressure should be sufficient to effectively disseminate the particles throughout the retina through a spraying or jetting action, but not sufficient to substantially damage retinal tissue. In one embodiment, a pressure may range from 0.0001 psi to 100 psi. The pressurized spraying also assists in distributing particles that disseminate and localize throughout the retinal layers. Localization of the particles permits enhanced control, duration, ease, etc. of stimulating these particles, resulting in enhanced control and effect.

The particles are introduced into the interior lumen 158 from any source, such as from a reservoir chamber, a syringe, etc. (not shown), and are mixed with a carrier fluid 166 such as a biocompatible gas or liquid. As non-limiting examples, air, oxygen, nitrogen, sulfur hexafluoride other perfluorocarbon fluids, etc., alone or in combination, may be used.

The pressurized fluid carrying the particles is regulated for ejection from the outlet ports, and is propelled toward the retina. The diameter of the outlet ports and pressure of the fluid are such as to allow the particles to penetrate the retinal tissue with minimal or no retinal damage. To accomplish a wide distribution of the particles throughout the retinal layers, the pressure may be pulsed to vary the penetration depth of the particles. The cannula may also be rotated or moved to spray or cover a larger area of the retina. Those of ordinary skill in the art will recognize other ways to distribute the particles throughout the retinal layers. As one example, the diameter of the outlet ports may be varied to provide different penetration depths. The outlet port diameters may range from about 0.01 mm to about 1 mm. As another example, the angles of the outlet ports may be varied to provide different spray patterns.

The above-described device may be used in the inventive method to deliver particles to the retina and distribute them substantially throughout the retinal layers, both intracellularly and/or intercellularly. That is, the particles diffusively locate and penetrate the retinal layers.

In one embodiment, an ocular surgeon may remove the vitreous gel, such as by an aspiration probe having vacuum pressure or a cutting probe, and replacing the contents of the vitreous cavity with saline, air, or another biocompatible fluid to facilitate particle penetration. The spraying device is inserted through the incision and into the vitreous cavity. The distal end of the device is positioned on or adjacent the retina, with the surgeon verifying placement using an operating microscope, a slit lamp, or other methods known in the art. Once the distal end of the device is adequately positioned, the pressurized fluid stream carrying the particles is generated and the particles are propelled toward the retina so as to distribute the particles throughout the retinal layers, as previously described. A gas probe may also be inserted into the vitreous cavity, such as by a second incision, to maintain the desired intraocular pressure. In another embodiment, the vitreous gel is not removed and the particles are injected (e.g., using a needle or other type of injection device) without spraying close to the retina, where the particles then diffuse through intercellular spaces of the retina and throughout the eye. Those of ordinary skill in the art will recognize that while the delivery method has been described as using separate aspiration probes, fiber optic probes, and gas probes, a single device that accomplishes delivery of the particles to the retina, removal of the vitreous gel and gas delivery may be used in the inventive method.

Once located at the desired location, the particles are stimulated using an energy source. The energy source may be located external to the eye at either or both the front and back, external to the retina, or on the surface of the retina. Because the retina is transparent, light is able to pass through and hence activate the particles located on and in various retinal tissues, as is subsequently described. The activated particles reset or influence the plasma membrane electrical potential of excitable cells, resulting in a desired response in membrane polarity. As previously described, this may take the form of normalized polarization, repolarization, enhanced polarization (i.e., stimulation), or reduced polarization (i.e., calming), etc.

In one embodiment, the particles are delivered into the eye when the vitreous gel is removed and replaced with saline and the internal limiting membrane (ILM) is removed. In one embodiment, the internal limiting membrane is removed to permit particle dissemination within the retina and throughout retinal intracellular spaces. This enhances diffusion of particles in the retina so that, by fluid flow, particles can then disseminate and penetrate retinal layers. Particles may adhere to the outer cellular membrane and/or may enter retinal cells. The particle size and/or spraying pressure, location, formulation may be altered to aid in selectivity. Particle penetration may be limited by the external limiting membrane (ELM), which may act as a semi-barrier to retinal transport. Excess particles may be removed as a part of the normal phagocytosis process (e.g., by glial cells). Ganglial cells in the eye, responsible for visual processing (discerning motion, depth, fine shapes, textures, colors), have less active phagocytosis mechanisms, so treatment of these cells may be affected by spraying to minimize excess distribution of particles.

Repolarization of cell membranes in a first location may have beneficial effects on polarization of cell membranes in second and subsequent locations. Due to propagation of electrical stimuli, a wave of electrical distribution is disseminated throughout the retina, for example, along a glial cell network. Because the glial cells assist in maintaining electrical balance, propagation also stabilizes polarization of adjacent cells.

It will be appreciated from the above description that stimulation of the entire retina may be achieved, rather than stimulation of a portion of the retina in proximity to a fixed electrode. This achieves substantially uniform repolarization, minimizing or preventing areas of hyper- and/or hypopolarization, which assist in functional regeneration of glial cells.

In one embodiment, an ocular surgeon may stimulate the particles with an external light source, by ambient light, by ultrasound radiation, or by other mechanisms known to one skilled in the art. The particles facilitate, enhance, or boost a biological cell's regulation of its polarity, with adjacent cells capable of being stimulated due to the glial stimulus-propagating network.

Each of the following references is expressed incorporated by reference herein in its entirety:

Bakalova et al. Quantum Dot-Conjugated Hybridization Probes for Preliminary Screening of siRNA Sequences. J. Am. Chem. Soc. 127 (2005) 11328-11335.

Derfus et al. Targeted Quantum Dot Conjugates for siRNA Delivery. Bioconjugate Chem. 18 (2007) 1391-1396.

Deisseroth, Optogenetics, Nature Methods, published online Dec. 20, 2010, available at http://www.stanford.edu/group/dlab/papers/deisserothnature2010.pdf.

Dixit et al. Quantum Dot Encapsulation in Viral Capsids. Nano Letters, 6 (2006) 1993-1999.

Ebenstein et al. Combining atomic force and fluorescence microscopy for analysis of quantum-dot labeled protein-DNA complexes. J. Molecular Recognition, 22 (2009) 397-402.

Gill et al. Fluorescence Resonance Energy Transfer in CdSe/ZnS-DNA Conjugates: Probing Hybridization and DNA Cleavage. J. Phys. Chem. B, 109 (2005) 23715-23719.

Huang et al. Intermolecular and Intramolecular Quencher Based Quantum Dot Nanoprobes for Multiplexed Detection of Endonuclease Activity and Inhibition. Anal. Chem. 83 (2011) 8913-8918.

Joo et al. Enhanced Real-Time Monitoring of Adeno-Associated Virus Trafficking by Virus-Quantum Dot Conjugates. ACS Nano 5 (2011) 3523-3525.

Lim et al. Specific Nucleic Acid Detection Using Photophysical Properties of Quantum Dot Probes. Anal. Chem. 82 (YEAR) 886-891.

Mossman, Quantum dots track who gets into cell nucleus. Physorg.com, Sep. 2, 2010 http://www.physorg.com/news202628740.html Sarkar et al. Doped Semiconductor Nanocrystals and Organic Dyes: An Efficient and Greener FRET System J. Phys. Chem. Lett. 1 (2010) 636-640.

Suzuki et al. Quantum Dot FRET Biosensors that Respond to pH, to Proteolytic or Nucleolytic Cleavage, to DNA Synthesis, or to a Multiplexing Combination. J. American Chemical Society 130 (2008) 5720-5725.

Wang et al. Nucleic Acid Conjugated Nanomaterials for Enhanced Molecular Recognition. ACS Nano 3 (2009) 2451-2460.

You et al. Incorporation of quantum dots on virus in polycationic solution. Int. J. Nanomedicine 1 (2006) 59-64.

Audero et al. Sporadic Autonomic Dysregulation and Death Associated with Excessive Serotonin Autoinhibition. Science 321 (2008) 130-133.

De Crespigny et al. Magnetic Resonance Imaging Assessment of Cerebral Hemodynamics During Spreading Depression in Rats. Journal of Cerebral Blood Flow and Metabolism 18 (1998) 1008-1017.

Höhne et al. Acetazolamide prevents hypoxic pulmonary vasoconstriction in conscious dogs. J. Appl. Physiol. 97 (2004), pp. 515-521.

Other variations or embodiments of the invention will also be apparent to one of ordinary skill in the art from the above description. As one example, other forms, routes, and sites of administration are contemplated. As another example, the invention may be used in patients who have experienced ocular trauma, retinal degeneration, ischemia, inflammation, etc. As another example, the particles may include sensing devices for qualitative and/or quantitative chemistry or other determinations. For example, the particles may include sensors or other detection means for glucose, oxygen, glycosylated hemoglobin, proteins including but limited to enzymes, pressure, indicators for retinal degenerative disease, etc. Thus, the forgoing embodiments are not to be construed as limiting the scope of this invention.

What is claimed is:

1. A method for providing and/or monitoring therapy for a condition in a patient, the method comprising
administering to the patient having a genetic or acquired degenerative disease a complex comprising a quantum dot coated with a biocompatible molecule for cell uptake without reliance on a viral vector and conjugated with a cell penetrating agent and a plurality of genes, the first one of the plurality of genes for correcting the genetic or acquired degenerative disease, the first one of the plurality of genes selected from the group consisting of a gene encoding an enzyme, a gene encoding a synthetic enzyme, a gene encoding a trophic factor selected from the group consisting of BDNF, CNTF, NGF, IGF, GMF, FGFα, FGFβ, NT3, NT5, and pleiotrophin, a gene encoding an apolipoprotein selected from the group consisting of ApoAI, ApoAIV, and ApoE, a gene encoding a dystrophin, a gene encoding a minidystrophin, a gene encoding a protein participating in DNA repair, a suicide gene, a gene encoding a cytosine deaminase, a pro-apoptotic gene, a gene encoding a prodrug converting enzyme, a gene encoding a heat shock protein, a gene encoding a telomerase, a gene encoding an immunosuppressive protein, a gene encoding a Bruton's tyrosine kinase, a gene encoding an ADA, a gene encoding an SMN-1, a gene encoding a Rab-Escort Protein (REP-1), a gene encoding an RPE-specific 65-kDA protein (RPE65), a gene encoding MERTK, a gene encoding ABC4, and a gene encoding MYO7A; the complex injected with a biocompatible fluid for, without reliance on a viral vector, correcting the genetic or acquired degenerative disease;
delivering the plurality of genes to a target cell using the quantum dot of the complex as a carrier; and
stimulating the quantum dot of the complex with an energy source after one or more genes of the target cell have been modified by the first one of the plurality of genes carried by the quantum dot so as to regulate the action potential of the cell membrane of the target cell.

2. The method of claim 1 where light is applied as the energy source to controllably activate the cell target membrane by controlling at least one of exposure time, exposure intensity, and exposure site.

3. The method of claim 1 where the biocompatible molecule is directly or indirectly associated with, or covalently conjugated to, the quantum dot.

4. The method of claim 1 where the therapy is curative, palliative, or remediative, and is either therapeutic or preventive.

5. The method of claim 1 further comprising an additional therapy selected from the group consisting of stem cell therapy, immunomodulators, anti-integrins, anti-inflammatory agents, antibiotics, anti-viral agents, anti-fungal agents, anti-proliferative agents, and anti-cancer agents.

6. The method of claim 1 where the condition is selected from the group consisting of a degenerative retinal disease, a degenerative CNS disease, and a degenerative cardiovascular disease.

7. The method of claim 1 where the complex is targeted and/or directed to a specific region of the body selected from a specific organ, tissue type, and/or cell type, where the targeted location is the site of the genetic or acquired degenerative disease or a location affected by the genetic or acquired degenerative disease.

8. The method of claim 1 where the quantum dot contains or is provided with a coating to enhance or impart biocompatibility and/or cell selectivity using an antibody or a receptor that directs the complex to the target.

9. The method of claim 1 where when the genetic or acquired degenerative disease is an ocular genetic or acquired degenerative disease, the complex is injected intravitreally or introduced into the cornea, choroid, or retina, and the ocular genetic or acquired degenerative disease is selected from the group consisting of retinitis pigmentosa and choroideremia x-linked retinoschisis.

10. The method of claim 1, wherein the genetic or acquired degenerative disease is selected from the group consisting of spinal muscular dystrophy, muscular dystrophy, diminished cell survival, X-linked agammaglobulinemia, adenosine deaminase severe combined immunodeficiency (ADA SCID), spinal muscular atrophy, choroideremia, Leber's congenital amaurosis (LCA), retinitis pigmentosa, and Usher's syndrome type 1B.

11. The method of claim 1 further comprising imaging the complex by a method selected from the group consisting of photography, optical coherence tomography (OCT), magnetic resonance imaging (MRI), spectroscopy, microscopy of a body fluid or tissue, and combinations thereof.

12. The method of claim 11 where the complex comprises a targeting moiety and the diagnosis of the genetic or acquired degenerative disease in the patient is based on at least one of complex concentration or complex localization at the target site in the patient.

13. The method of claim 1 where the complex further comprises a magnetic or paramagnetic nanoparticle facilitating introduction of the complex into the target cell.

14. The method of claim 1, wherein the complex further comprises a magnetic and/or paramagnetic nanoparticle conjugated with a targeting agent.

15. The method of claim 1 where the biocompatible molecule for cell uptake is selected from the group consisting of an antibody, a ligand for a receptor, and combinations thereof.

16. The method of claim 14 where the quantum dot ranges from about 3 nm to about 50 nm and the magnetic or paramagnetic nanoparticle ranges from about 70 nm to about 200 nm.

17. The method of claim 14 further comprising applying at least one of an alternating magnetic field or electromagnetic radiation resulting in a temperature increase in the magnetic or paramagnetic nanoparticles that sufficiently perturbs the cell membrane of the target cell to result in facilitated entry of the complex via the perturbed membrane.

18. The method of claim 14 further comprising the quantum dot associated with a thermosensitive polymer forming a thermosensitive quantum dot that, upon application of an external energy source, results in a temperature increase in the quantum dot to about 39° C. to about 43° C. facilitating release of the biocompatible molecule from the thermosensitive quantum dot.

19. The method of claim 1 where the complex comprises a quantum dot of a first size and a quantum dot of a second size different from that of the first size, at least one size of the quantum dot having enhanced susceptibility to an external energy source capable of increasing the temperature of the enhanced susceptibility quantum dot, the increase in temperature providing enhanced access to the target cell.

20. The method of claim 1 further comprising implanting an apparatus in the patient to provide localized internal activation of the complex, the apparatus providing the energy source for stimulating the quantum dot of the complex.

21. The method of claim 20 where the apparatus comprises an LED light source and a rechargeable battery, and the light source provides a light pulse activating the complex.

22. The method of claim 21 where the light source further comprises a fiber optic tube or a flexible silicone tube to direct the light to a desired area(s).

23. The method of claim 1 where the complex comprises at least a first and a second quantum dot where the first and the second quantum dots absorb energy at different wavelengths, and the first and second particles are activated by different wavelengths.

24. The method of claim 23 where selective activity of the complex is by selective wavelength exposure.

25. The method of claim 1 where the quantum dot is made from organic molecules selected from the group consisting of organic nanocrystal and crystalline forms of carbon.

26. The method of claim 25 where the crystalline form of carbon is selected from the group consisting of fullerene, graphene, carbon nanotube, and combinations thereof.

27. The method of claim 25 where the quantum dot is coated with at least one of organic molecule, biocompatible protein, peptide, phospholipid, polymer, and polyethylene glycol polymers, the coating increasing biocompatibility of the quantum dot.

28. A method for providing and/or monitoring therapy for a condition in a patient, the method comprising
  administering to the patient having a genetic or acquired degenerative disease a complex comprising
    a magnetic or paramagnetic nanoparticle conjugated with a targeting moiety, and
    a quantum dot coated with a biocompatible molecule for target cell uptake without reliance on a viral vector and conjugated with a cell penetrating agent and a gene selected from the group consisting of a rhodopsin gene, a channelrhodopsin gene, and a halorhodopsin gene, the complex injected with a biocompatible fluid for, without reliance on a viral vector, building a light activated rhodopsin channel in the target cell membrane and correcting the genetic or acquired degenerative disease so that the target cell can be stimulated by an external or an internal light,
  to result in repolarizing, hyperpolarizing, or creating an action potential in the target cell;
  delivering the gene to the target cell using the quantum dot of the complex as a carrier;

applying at least one of an alternating magnetic field or electromagnetic radiation resulting in a temperature increase in the magnetic or paramagnetic nanoparticle that sufficiently perturbs the cell membrane of the target cell to result in facilitated entry of the complex via the perturbed cell membrane; and stimulating the quantum dot of the complex with the external or internal light after one or more genes of the target cell have been modified by the gene carried by the quantum dot so as to activate the rhodopsin, channelrhodopsin, or halorhodopsin produced by the one or more modified genes of the target cell, thereby silencing the target cell or enhancing the action potential of the target cell.

29. The method of claim 28, further comprising the quantum dot associated with a thermosensitive polymer forming a thermosensitive quantum dot that, upon application of an external energy source, results in a temperature increase in the quantum dot to about 39° C. to about 43° C. facilitating release of the biocompatible molecule from the thermosensitive quantum dot.

* * * * *